(12) United States Patent
Wang et al.

(10) Patent No.: US 11,028,382 B2
(45) Date of Patent: *Jun. 8, 2021

(54) LYOPHILIZED FORMULATIONS FOR FACTOR XA ANTIDOTE

(71) Applicant: Portola Pharmaceuticals, Inc., South San Francisco, CA (US)

(72) Inventors: Juan Wang, Foster City, CA (US); Gregory A. Sacha, Bargersville, IN (US); Phuong M. Nguyen, Burlingame, CA (US)

(73) Assignee: Alexion Pharmaceuticals, Inc., Boston, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/895,448

(22) Filed: Jun. 8, 2020

(65) Prior Publication Data
US 2020/0299668 A1 Sep. 24, 2020

Related U.S. Application Data

(60) Division of application No. 15/820,265, filed on Nov. 21, 2017, which is a continuation of application No. 15/136,810, filed on Apr. 22, 2016, now abandoned, which is a continuation of application No. PCT/US2015/046173, filed on Aug. 20, 2015.

(60) Provisional application No. 62/039,809, filed on Aug. 20, 2014.

(51) Int. Cl.
| | | |
|---|---|---|
| *A61K 38/00* | (2006.01) | |
| *C12N 9/64* | (2006.01) | |
| *A61K 9/00* | (2006.01) | |
| *A61K 47/18* | (2017.01) | |
| *A61K 47/26* | (2006.01) | |
| *A61K 9/19* | (2006.01) | |
| *A61K 38/48* | (2006.01) | |
| *C07K 14/00* | (2006.01) | |

(52) U.S. Cl.
CPC .......... *C12N 9/6432* (2013.01); *A61K 9/0019* (2013.01); *A61K 9/19* (2013.01); *A61K 38/4846* (2013.01); *A61K 47/183* (2013.01); *A61K 47/26* (2013.01); *C07K 14/00* (2013.01); *C12Y 304/21006* (2013.01)

(58) Field of Classification Search
None
See application file for complete search history.

(56) References Cited

U.S. PATENT DOCUMENTS

| | | | |
|---|---|---|---|
| 5,883,077 A | 3/1999 | Brunck et al. | |
| 6,586,574 B1 | 7/2003 | Hansen et al. | |
| 8,153,590 B2 * | 4/2012 | Lu | A61K 47/60 514/14.4 |
| 9,056,106 B2 * | 6/2015 | Sinha | A61P 39/00 |
| 9,388,401 B2 * | 7/2016 | Lu | A61K 38/4833 |
| 2004/0180827 A1 | 9/2004 | Chen et al. | |
| 2009/0098119 A1 | 4/2009 | Lu et al. | |
| 2010/0255000 A1 | 10/2010 | Sinha et al. | |
| 2011/0015128 A1 | 1/2011 | Sinha et al. | |
| 2011/0178019 A1 | 7/2011 | Rippner et al. | |
| 2012/0121580 A1 * | 5/2012 | Bhambhani | A61K 47/183 424/130.1 |
| 2013/0252979 A1 | 9/2013 | Meier et al. | |
| 2016/0237420 A1 | 8/2016 | Wang et al. | |

FOREIGN PATENT DOCUMENTS

| | | | |
|---|---|---|---|
| CA | 2362927 | 7/2011 | |
| WO | WO 2000/48635 | 8/2000 | |
| WO | WO 2011/008885 | 1/2011 | |
| WO | WO-2011008885 A1 * | 1/2011 | .......... A61K 9/0019 |
| WO | WO 2011/017070 | 2/2011 | |
| WO | WO 2011/131720 | 10/2011 | |
| WO | WO 2011/088152 | 11/2011 | |
| WO | WO 2013/049804 | 4/2013 | |

OTHER PUBLICATIONS

Extended European Search Report for EP Appl. No. 15834421.8 dated Dec. 15, 2017, 11 pages.
Garidel. Protein Solubility from a Biochemical Physicochemical and Colloidal Perspective. American Pharm Rev. Dec. 30, 2013, 10 pages.
Ghosh et al., "Method for enhancing solubility of the expressed recombinant proteins in *Escherichia coli*", BioTechniques 37:418-423, Sep. 2007.
International Search Report and Written Opinion for PCT/US2015/046173 dated Dec. 21, 2015 (2 pages).
International Search Report and Written Opinion for PCT/US2017/019502 dated May 31, 2017, 10 pages.
Japan Pharmaceutical Excipient Council, ed. "iyakuhintenkabutsujiten" 2007 (pharmaceutical excipients dictionary), Yakuji Nippo Limited, Jul. 25, 2007, p. 274.
Ken-ichi Izutsu. Stabilization of Therapeutic Proteins by Chemical and Phsical Methods. Therapeutic Proteins, Edited by Smales and James, 2005, Humana Press, Chapter 22, pp. 287-292.
Padmanabhan et al., "Structure of Human des(1-45) Factor Xa at 2.2 A Resolution", Journal Mol. Biol., 1993, 232:947-966.
Registry No. 1262449-58-0 Information, Feb. 2011, 2 pages.

\* cited by examiner

*Primary Examiner* — Satyanarayana R Gudibande
(74) *Attorney, Agent, or Firm* — Sheppard Mullin Richter & Hampton LLP

(57) ABSTRACT

The present disclosure relates to solutions and methods of preparing lyophilized formulations of factor Xa (fXa) antidotes. A suitable aqueous formulation suitable for lyophilization can include a fXa antidote, a solubilizing agent, a stabilizer, and a crystalline component, wherein the formulation does not collapse during lyophilization.

9 Claims, 12 Drawing Sheets
Specification includes a Sequence Listing.

LYOPHILIZED FORMULATIONS FOR FACTOR XA ANTIDOTE

CROSS-REFERENCE TO RELATED PATENT APPLICATIONS

This application is a division of U.S. application Ser. No. 15/820,265 filed Nov. 21, 2017, which is a continuation of U.S. application Ser. No. 15/136,810 filed Apr. 22, 2016, which is a continuation of International Application No. PCT/US2015/046173, filed Aug. 20, 2015, which claims the benefit under 35 U.S.C. § 119(e) of U.S. Provisional Application 62/039,809, filed Aug. 20, 2014, the content of each of which is incorporated herein by reference in its entireties and for all purposes.

BACKGROUND

Anticoagulants serve a need in the marketplace in treatment or prevention of undesired thrombosis in patients with a tendency to form blood clots, such as, for example, those patients having clotting disorders, confined to periods of immobility or undergoing medical surgeries. One of the major limitations of anticoagulant therapy, however, is the bleeding risk associated with the treatments, and limitations on the ability to rapidly reverse the anticoagulant activity in case of overdosing or if an urgent surgical procedure is required. Thus, specific and effective antidotes to all forms of anticoagulant therapy are highly desirable.

Delivery of biologically active proteins by injection is generally the delivery route of choice when oral delivery is not practical or an immediate therapeutic activity is required. However, biological, chemical, and physical barriers such as poor long-term storage, osmolality, solubility, and stability make delivery of biologically active agents by injection to mammals problematic. Lyophilization can solve long-term storage issues. Nevertheless, there are problems that also occur with lyophilization, such as poor solubility and stability of the lyophilate. Therefore, there exists a need for improved injectable preparations of antidotes to anticoagulants, which are stable and soluble. The disclosure satisfies these and other needs.

Any and all publications, patents, patent applications mentioned herein are hereby incorporated by reference in their entirety.

SUMMARY

The present disclosure provides lyophilized formulations for a derivative of the factor Xa (fXa) protein, referred to as the "r-Antidote." Compared to the wild-type fXa protein, the r-Antidote has modifications to the Gla domain and the active site, retains fXa's ability to bind to a fXa inhibitor but does not assemble into a prothrombinase complex. The r-Antidote is a two-chain polypeptide (see SEQ ID NO. 3 in Table 3, which includes a light chain (SEQ ID NO. 4) and a heavy chain (SEQ ID NO. 5) connected with a single disulfide bond between Cysteine 98 (Cys98) of the light chain and Cysteine 108 (Cys108) of the heavy chain.

Also like the wild-type fXa, the r-Antidote undergoes post-translational modifications resulting in glycosylation at certain amino acid residues, e.g., Ser56, Ser72, Ser76 and Thr82 of the light chain and Thr249 of the heavy chain, and a modified residue, (3R)-3-hydroxyAsp at Asp29 of the light chain. Further, in addition to the inter-chain disulfide bond, there are intra-chain disulfide bonds formed between Cysteines 16 and 27, 21 and 36, 38 and 47, 55 and 66, 62 and 75, and 77 and 90 of the light chain, and between Cysteines 7 and 12, 27 and 43, 156 and 170, and 181 and 209 of the heavy chain.

Given the two-chain structure and various post-translational modifications of the r-Antidote, it is shown herein that development of a stable lyophilized formulation that provides a stable and soluble solution with an acceptable osmolality presents a great challenge. Unexpectedly, however, the present inventors were able to arrive at a solution that balances protein solubility, stability, cake structure and osmolality.

In one embodiment, the present disclosure provides an aqueous formulation. In one embodiment, the formulation comprises from 10 mM to 55 mM arginine or from 8 mM to 35 mM citrate, from 1% to 3% sucrose (w/v), from 2% to 8% mannitol (w/v) and at least 5 mg/mL of a two-chain polypeptide comprising a first chain of the amino acid sequence of SEQ ID NO. 4, a second chain of the amino acid sequence of SEQ ID NO. 5, and a disulfide bond between a first Cysteine residue at position 98 (Cys98) of SEQ ID NO. 4 and a second Cysteine residue at position 108 (Cys108) of SEQ ID NO. 5, wherein the formulation has a pH from 7.5 to 8.

In some aspects, the formulation comprises from 40 mM to 50 mM arginine, from 1.5% to 2.5% sucrose (w/v), from 4.5% to 5.5% mannitol (w/v) and at least 10 mg/mL of the polypeptide. In some aspects, the formulation comprises from 10 mM to 30 mM citrate, from 1.5% to 2.5% sucrose (w/v), from 4.5% to 5.5% mannitol (w/v) and at least 10 mg/mL of the polypeptide.

In some aspects, the formulation comprises from 40 mM to 50 mM arginine, from 1.5% to 2.5% sucrose (w/v), from 4.5% to 5.5% mannitol (w/v) and at least 18, 19 or 20 mg/mL of the polypeptide. In some aspects, the formulation comprises from 10 mM to 30 mM citrate, from 1.5% to 2.5% sucrose (w/v), from 4.5% to 5.5% mannitol (w/v) and at least 10 mg/mL of the polypeptide.

In some aspects, the formulation comprises about 45 mM arginine, about 2% sucrose (w/v), about 5% mannitol (w/v) and about 10 mg/mL of a two-chain polypeptide comprising a first chain comprising the amino acid sequence of SEQ ID NO. 4, a second chain comprising the amino acid sequence of SEQ ID NO. 5, and a disulfide bond between a first Cysteine residue at position 98 (Cys98) of SEQ ID NO. 4 and a second Cysteine residue at position 108 (Cys108) of SEQ ID NO. 5, wherein the formulation has a pH of about 7.8. In one aspect, the formulation further includes polysorbate 80 (0.01% w/v to 0.02% w/v) and/or a buffer.

In some aspects, the formulation comprises about 45 mM arginine, about 2% sucrose (w/v), about 5% mannitol (w/v) and about 20 mg/mL of a two-chain polypeptide comprising a first chain comprising the amino acid sequence of SEQ ID NO. 4, a second chain comprising the amino acid sequence of SEQ ID NO. 5, and a disulfide bond between a first Cysteine residue at position 98 (Cys98) of SEQ ID NO. 4 and a second Cysteine residue at position 108 (Cys108) of SEQ ID NO. 5, wherein the formulation has a pH of about 7.8. In one aspect, the formulation further includes polysorbate 80 (0.01% w/v to 0.02% w/v) and/or a buffer.

In some aspects, the polypeptide comprises an amino acid residue that is modified to be different from natural amino acids. In some aspects, residue Asp29 of the first chain is modified to (3R)-3-hydroxyAsp at Asp29. In some aspects, the polypeptide comprises at least an intra-chain disulfide bond for each of the first and second chains.

Also provided, in one embodiment, is a method of preparing a lyophilized formulation of a two-chain polypeptide comprising a first chain of the amino acid sequence of SEQ ID NO. 4, a second chain of the amino acid sequence of SEQ ID NO. 5, and a disulfide bond between a first Cysteine residue at position 98 (Cys98) of SEQ ID NO. 4 and a second Cysteine residue at position 108 (Cys108) of SEQ ID NO. 5, comprising lyophilizing the aqueous formulation as describe above.

Another embodiment provides a lyophilized composition prepared by lyophilizing the aqueous formulation of the present disclosure.

In one embodiment, the present disclosure provides a lyophilized composition comprising at least 10% (w/w) of a two-chain polypeptide comprising a first chain of the amino acid sequence of SEQ ID NO. 4, a second chain of the amino acid sequence of SEQ ID NO. 5, and a disulfide bond between a first Cysteine residue at position 98 (Cys98) of SEQ ID NO. 4 and a second Cysteine residue at position 108 (Cys108) of SEQ ID NO. 5, and arginine:sucrose:mannitol in a weight ratio of the range (0.6-0.95):(1-3):(2-8), or alternatively L-arginine HCl:sucrose:mannitol in a weight ratio of the range (0.5-1.4):(1-3):(2-8).

In some aspects, the lyophilized composition comprises at least 15%, 16%, 17%, 18% or 19% (w/w) of the two-chain polypeptide. In some aspects, the weight ratio of L-arginine HCl:sucrose:mannitol is in the range of (0.9-1):(1.5-2.5):(4.5-5.5).

Also provided is a lyophilized composition comprising at least 10% (w/w) of a two-chain polypeptide comprising a first chain of the amino acid sequence of SEQ ID NO. 4, a second chain of the amino acid sequence of SEQ ID NO. 5, and a disulfide bond between a first Cysteine residue at position 98 (Cys98) of SEQ ID NO. 4 and a second Cysteine residue at position 108 (Cys108) of SEQ ID NO. 5, and citrate:sucrose:mannitol in a weight ratio of the range (0.15-0.66):(1-3):(2-8). In some aspects, the lyophilized composition comprises at least 10%, 15%, 16%, 17%, 18%, or 19% (w/w) of the two-chain polypeptide. In some aspects, the weight ratio of citrate:sucrose:mannitol is in the range of (0.19-0.57):(1.5-2.5):(4.5-5.5).

Another embodiment of the present disclosure provides a solution prepared by dissolving the lyophilized composition of the disclosure. In some aspects, the solvent is water or saline.

Yet another embodiment provides a method of reducing bleeding in a subject undergoing anticoagulant therapy with a factor Xa inhibitor comprising administering to the subject an effective amount of a solution of the disclosure. In some aspects, the factor Xa inhibitor is apixaban, rivaroxaban or betrixaban.

Still, also provided, in one embodiment, is an aqueous formulation, comprising a polypeptide comprising the amino acid sequence of SEQ ID NO. 3 or an amino acid sequence having at least 95% sequence identity to SEQ ID NO. 3, a solubilizing agent, a stabilizer, and a crystalline component, wherein the formulation does not collapse during lyophilization.

In some aspects, the crystalline component is mannitol. In some aspects, the mannitol is present in a concentration from 2% to 8% (w/v). In some aspects, the solubilizing agent is arginine or citrate and the stabilizer is sucrose. In some aspects, the aqueous formulation further comprises a surfactant and a buffer. In some embodiments, provided is a lyophilized composition prepared by lyophilizing the aqueous formulation.

DETAILED DESCRIPTION

I. Definitions

Figure 1A:
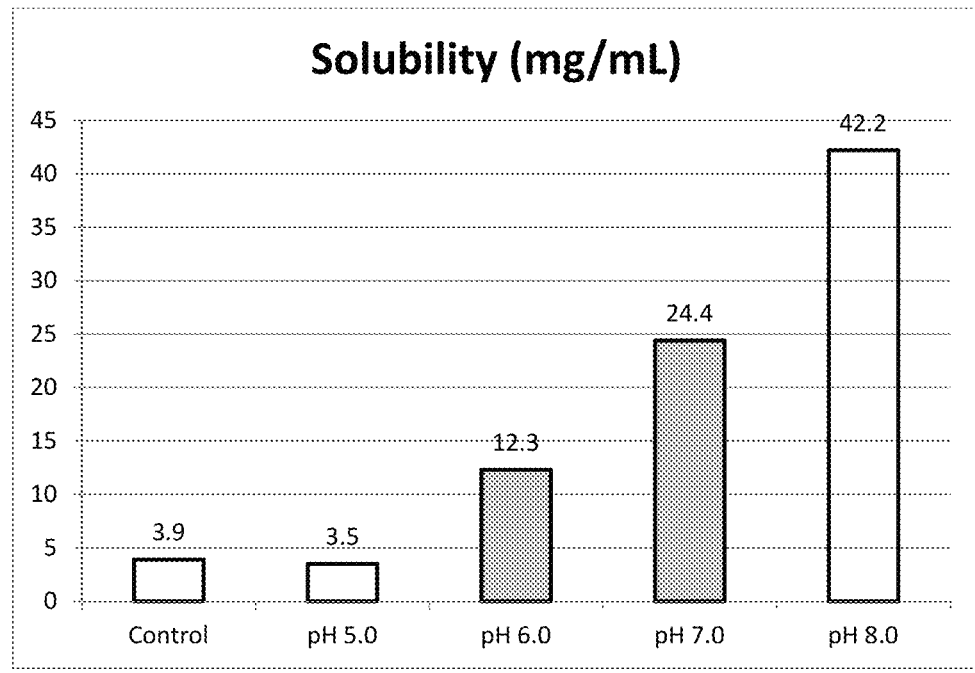
FIG. 1A-F are charts showing the solubility of the r-Antidote under different conditions (pH, solubilizing agent, ionic strength). Shaded bars indicate that protein precipitation was observed and empty bars indicate that no protein precipitation was observed.

All numerical designations, e.g., pH, temperature, time, concentration, and molecular weight, including ranges, are approximations which are varied (+) or (−) by increments of 0.1 or 10%. It is to be understood, although not always explicitly stated that all numerical designations are preceded by the term "about". It also is to be understood, although not always explicitly stated, that the reagents described herein are merely exemplary and that equivalents of such are known in the art.

As used in the specification and claims, the singular form "a", "an" and "the" include plural references unless the context clearly dictates otherwise. For example, the term "a pharmaceutically acceptable carrier" includes a plurality of pharmaceutically acceptable carriers, including mixtures thereof.

As used herein, the term "comprising" is intended to mean that the compositions and methods include the recited elements, but do not exclude others. "Consisting essentially of" when used to define compositions and methods, shall mean excluding other elements of any essential significance to the combination for the intended use. Thus, a composition consisting essentially of the elements as defined herein would not exclude trace contaminants from the isolation and purification method and pharmaceutically acceptable carriers, such as phosphate buffered saline, preservatives, and the like. "Consisting of" shall mean excluding more than trace elements of other ingredients and substantial method steps for administering the compositions of this disclosure. Embodiments defined by each of these transition terms are within the scope of this disclosure.

The term "protein" and "polypeptide" are used interchangeably and in their broadest sense to refer to a compound of two or more subunit amino acids, amino acid analogs or peptidomimetics. The subunits may be linked by peptide bonds. In another embodiment, the subunit may be linked by other bonds, e.g., ester, ether, etc. A protein or peptide must contain at least two amino acids and no limitation is placed on the maximum number of amino acids which may comprise a protein's or peptide's sequence. As used herein the term "amino acid" refers to either natural and/or unnatural or synthetic amino acids, including glycine and both the D and L optical isomers, amino acid analogs and peptidomimetics. Single letter and three letter abbreviations of the naturally occurring amino acids are listed below.

"Factor Xa" or "fXa" or "fXa protein" is a serine protease in the blood coagulation pathway, which is produced from the inactive factor X (fX, SEQ ID NO. 1, Table 1). The nucleotide sequence coding human factor X ("fX") can be found in GenBank with accession number "NM_000504." Upon catalytic cleavage of the first 52 residues of the heavy chain, fX is activated to fXa. FXa contains a light chain and a heavy chain. The first 45 amino acid residues (residues 1-45 of SEQ ID NO. 1) of the light chain is called the Gla domain because it contains 11 post-translationally modified γ-carboxyglutamic acid residues (Gla). It also contains a short (6 amino acid residues) aromatic stack sequence (residues 40-45 of SEQ ID NO. 1). Chymotrypsin digestion selectively removes the 1-44 residues resulting in Gla-domainless fXa. The serine protease catalytic domain of fXa locates at the C-terminal heavy chain. The heavy chain of fXa is highly homologous to other serine proteases such as thrombin, trypsin, and activated protein C.

"Native fXa" or "wild-type fXa" refers to the fXa naturally present in plasma or being isolated in its original, unmodified form, which processes the biological activity of activating prothrombin therefore promoting formation of blood clot. The term includes naturally occurring polypeptides isolated from tissue samples as well as recombinantly produced fXa. "Active fXa" refers to fXa having the procoagulant activity of activating prothrombin. "Active fXa" may be a native fXa or modified fXa that retains procoagulant activity.

As used herein, "fXa derivatives" refer to modified fXa proteins that do not compete with fXa in assembling into the prothrombinase complex and have reduced or no procoagulant or catalytic activities, and yet bind and/or substantially neutralize the anticoagulants, such as fXa inhibitors. "Procoagulant activity" of an fXa protein or fXa derivative, in some aspects, refers to the enzymatic activity that the wild-type active fXa polypeptide carries. Examples of fXa derivatives are provided in U.S. Pat. No. 8,153,590, and PCT publications WO2009/042962 and WO2010/056765, and further provided herein, such as SEQ ID NO: 2 and 3 and biological equivalents thereof.

The "enzymatic activity" of an fXa polypeptide or derivatives thereof refers to the polypeptide's ability to catalyze a biochemical reaction with a substrate through direct interaction with the substrate.

SEQ ID NO: 2 contains 3 mutations relative to the wild type fXa. The first mutation is the deletion of 6-39 aa in the Gla-domain of fX. The second mutation is replacing the activation peptide sequence 143-194 aa with -RKR-. This produces a -RKRRKR- (SEQ ID NO: 6) linker connecting the light chain (SEQ ID NO: 4) and the heavy chain (SEQ ID NO: 5). Upon secretion, this linker is cleaved resulting in a two-chain polypeptide, SEQ ID NO: 3 (r-Antidote). The third mutation is mutation of active site residue S379 to an Ala residue. This amino acid substitution corresponds to amino acid 296 and 290 of SEQ ID NOS: 1 and 3, respectively.

The term "r-Antidote" refers to a processed two-chain polypeptide processing product of SEQ ID NO: 2, after cleavage of the linker. This is represented by SEQ ID NO: 3. The r-antidote is disclosed in, e.g., U.S. Pat. No. 8,153,590, the content of which is incorporated to the present disclosure by reference. The r-Antidote includes a light chain (SEQ ID NO. 4) and a heavy chain (SEQ ID NO. 5) connected with a single disulfide bond between Cysteine 98 (Cys98) of the light chain and Cysteine 108 (Cys108) of the heavy chain. Like the wild-type fXa, in certain production batches, the r-Antidote undergoes post-translational modifications resulting in glycosylation at certain amino acid residues, e.g., Ser56, Ser72, Ser76 and Thr82 of the light chain and Thr249 of the heavy chain, and a modified residue, (3R)-3-hydroxyAsp at Asp29 of the light chain. Further, in addition to the inter-chain disulfide bond, there can be intra-chain disulfide bonds formed between Cysteines 16 and 27, 21 and 36, 38 and 47, 55 and 66, 62 and 75, and 77 and 90 of the light chain, and between Cysteines 7 and 12, 27 and 43, 156 and 170, and 181 and 209 of the heavy chain.

TABLE 1

Polypeptide Sequence of Inactive Human Factor X (SEQ ID NO: 1)

| | | | | |
|---|---|---|---|---|
| 1 | ANSFLEEMKK | GHLERECMEE | TCSYEEAREV | FEDSDKTNEF |
| | WNKYKDGDQC | ETSPCQNQGK | | |
| 61 | CKDGLGEYTC | TCLEGFEGKN | CELFTRKLCS | LDNGDCDQFC |
| | HEEQNSVVCS | CARGYTLADN | | |
| 121 | GKACIPTGPY | PCGKQTLERR | KRSVAQATSS | SGEAPDSITW |
| | KPYDAADLDP | TENPFDLLDF | | |
| 181 | NQTQPERGDN | NLTRIVGGQE | CKDGECPWQA | LLINEENEGF |
| | CGGTILSEFY | ILTAAHCLYQ | | |

TABLE 1-continued

Polypeptide Sequence of Inactive Human Factor X (SEQ ID NO: 1)

241 AKRFKVRVGD RNTEQEEGGE AVHEVEVVIK HNRFTKETYD
    FDIAVLRLKT PITFRMNVAP

301 ACLPERDWAE STLMTQKTGI VSGFGRTHEK GRQSTRLKML
    EVPYVDRNSC KLSSSFIITQ

361 NMFCAGYDTK QEDACQGDSG GPHVTRFKDT YFVTGIVSWG
    EGCARKGKYG IYTKVTAFLK

421 WIDRSMKTRG LPKAKSHAPE VITSSPLK

TABLE 2

Polypeptide Sequence of the r-Antidote prior to removal of the-RKRRKR- (SEQ ID NO: 6) linker (SEQ ID NO: 2)

Light Chain (SEQ ID NO: 4)

1 ANSFL                                          F
  WNKYKDGDQC ETSPCQNQGK

61 CKDGLGEYTC TCLEGFEGKN CELFTRKLCS LDNGDCDQFC
   HEEQNSVVCS CARGYTLADN

121 GKACIPTGPY PCGKQTLER

Linker (SEQ ID NO: 6)

RKRRKR

Heavy Chain (SEQ ID NO: 5)

181             IVGGQE CKDGECPWQA LLINEENEGF
    CGGTILSEFY ILTAAHCLYQ

241 AKRFKVRVGD RNTEQEEGGE AVHEVEVVIK HNRFTKETYD
    FDIAVLRLKT PITFRMNVAP

301 ACLPERDWAE STLMTQKTGI VSGFGRTHEK GRQSTRLKML
    EVPYVDRNSC KLSSSFIITQ

361 NMFCAGYDTK QEDACQGDAG GPHVTRFKDT YFVTGIVSWG
    EGCARKGKYG IYTKVTAFLK

421 WIDRSMKTRG LPKAKSHAPE VITSSPLK

TABLE 3

Polypeptide Sequence of a Human Factor Xa triple mutant after removal of the -RKRRKR-(SEQ ID NO. 6) linker (SEQ ID NO: 3)

Light Chain (SEQ ID NO: 4)

1 ANSFL                                          F
  WNKYKDGDQC ETSPCQNQGK

61 CKDGLGEYTC TCLEGFEGKN CELFTRKLCS LDNGDCDQFC
   HEEQNSVVCS CARGYTLADN

121 GKACIPTGPY PCGKQTLER

Heavy Chain (SEQ ID NO: 5)

181             IVGGQE CKDGECPWQA LLINEENEGF
    CGGTILSEFY ILTAAHCLYQ

241 AKRFKVRVGD RNTEQEEGGE AVHEVEVVIK HNRFTKETYD
    FDIAVLRLKT PITFRMNVAP

TABLE 3-continued

Polypeptide Sequence of a Human Factor Xa triple mutant after removal of the -RKRRKR-(SEQ ID NO. 6) linker (SEQ ID NO: 3)

301 ACLPERDWAE STLMTQKTGI VSGFGRTHEK GRQSTRLKML
    EVPYVDRNSC KLSSSFIITQ

361 NMFCAGYDTK QEDACQGDAG GPHVTRFKDT YFVTGIVSWG
    EGCARKGKYG IYTKVTAFLK

421 WIDRSMKTRG LPKAKSHAPE VITSSPLK

The present disclosure also provides a variety of biological equivalents of r-Antidote (or their precursors, represented by SEQ ID NO: 2), or alternatively polypeptides having certain sequence identity to SEQ ID NO: 3. In one aspect, such biological equivalents retain the structural characteristics of SEQ ID NO: 3, that is, a modified active site and a deleted or modified Gla domain. In another aspect, such biological equivalents retain the functional features of SEQ ID NO: 3, that is, not competing with fXa in assembling into the prothrombinase complex and having reduced or no procoagulant (e.g., enzymatic or catalytic) activities.

The term "active site" refers to the part of an enzyme or antibody where a chemical reaction occurs. A "modified active site" is an active site that has been modified structurally to provide the active site with increased or decreased chemical reactivity or specificity. Examples of active sites include, but are not limited to, the catalytic domain of human factor X comprising the 235-488 amino acid residues, and the catalytic domain of human factor Xa comprising the 195-448 amino acid residues. Examples of modified active site include, but are not limited to, the catalytic domain of human factor Xa comprising 195-448 amino acid residues in SEQ ID NO: 1 with at least one amino acid substitution at position Arg306, Glu310, Arg347, Lys351, Lys414, or Arg424.

A "composition" is intended to mean a combination of active agent and another compound or composition, inert (for example, a detectable agent or label) or active, such as an adjuvant.

A "pharmaceutical composition" is intended to include the combination of an active agent with a carrier, inert or active, making the composition suitable for diagnostic or therapeutic use in vitro, in vivo or ex vivo.

The term "lyophilized formulation" refers to a pharmaceutical formulation or composition comprising a polypeptide of interest that is freeze-dried.

As used herein, the term "bulking agent" refers to an ingredient that provides bulk to the lyophilized formulation. Examples of bulking agents include, without limitation, mannitol, trehalose, lactose, sucrose, polyvinyl pyrrolidone, sucrose, glucose, glycine, cyclodextrins, dextran, solid PEGs and derivatives and mixtures thereof. In one embodiment, a formlation of the present disclosure optionally includes a bulking agent.

As used herein, a "pharmaceutically acceptable cake" refers to a non-collapsed solid drug product remaining after lyophilization that has certain desirable characteristics, e.g. pharmaceutically acceptable, long-term stability, a short reconstitution time, an elegant appearance and maintenance of the characteristics of the original solution upon reconstitution. The pharmaceutically acceptable cake can be solid, powder or granular material. The pharmaceutically acceptable cake may also contain up to five percent water by weight of the cake.

As used herein, the term "lyophilization" or freeze drying refers to a process in which water is removed from a product after it is frozen and placed under a vacuum, allowing the ice to change directly from solid to vapor without passing through a liquid phase. The process consists of three separate, unique, and interdependent processes; freezing, primary drying (sublimation), and secondary drying (desorption). Methods for lyophilizing polypeptides used in this disclosure are described herein and well known in the art.

The term "buffer" as used herein denotes a pharmaceutically acceptable excipient, which stabilizes the pH of a pharmaceutical preparation. Suitable buffers are well known in the art and can be found in the literature. Pharmaceutically acceptable buffers comprise but are not limited to tris-buffers, arginine-buffers, histidine-buffers, citrate-buffers, succinate-buffers and phosphate-buffers. Independently from the buffer used, the pH can be adjusted with an acid or a base known in the art, e.g., succinic acid, hydrochloric acid, acetic acid, phosphoric acid, sulfuric acid and citric acid, succinate, citrate, tris base, histidine, histidine HCl, sodium hydroxide and potassium hydroxide. Suitable buffers include, without limitation, histidine buffer, 2-morpholinoethanesulfonic acid (MES), cacodylate, phosphate, acetate, succinate, and citrate. The concentration of the buffer can be between about 4 mM and about 60 mM, or alternatively about 4 mM to about 40 mM, or alternatively about 5 mM to about 25 mM.

"Cryoprotectants" are known in the art and include without limitation, e.g., sucrose, trehalose, and glycerol. A cryoprotectant exhibiting low toxicity in biological systems is generally used.

The term "tonicity agent" as used herein denotes pharmaceutically acceptable agents used to modulate the tonicity of the formulation. Isotonicity generally relates to the osmotic pressure relative to a solution, usually relative to that of human blood serum. A formulation can be hypotonic, isotonic or hypertonic. In one aspect, the formulation is isotonic. An isotonic formulation is liquid or liquid reconstituted from a solid form, e.g. from a lyophilized form and denotes a solution having the same tonicity as some other solution with which it is compared, such as physiologic salt solution and the blood serum. Suitable isotonicity agents include but are not limited to sodium chloride, potassium chloride, glycerin and any component from the group of amino acids, sugars, as defined herein as well as combinations thereof.

As used herein, the term "surfactant" refers to a pharmaceutically acceptable organic substance having amphipathic structures; namely, it is composed of groups of opposing solubility tendencies, typically an oil-soluble hydrocarbon chain and a water-soluble ionic group. Surfactants can be classified, depending on the charge of the surface-active moiety, into anionic, cationic, and nonionic surfactants. Surfactants are often used as wetting, emulsifying, solubilizing, and dispersing agents for various pharmaceutical compositions and preparations of biological materials. In some embodiments of the pharmaceutical formulations described herein, the amount of surfactant is described as a percentage expressed in weight/volume percent (w/v %). Suitable pharmaceutically acceptable surfactants include but are not limited to the group of polyoxyethylensorbitan fatty acid esters, polyoxyethylene alkyl ethers, alkylphenylpolyoxyethylene ethers, polyoxyethylene-polyoxypropylene copolymer, or sodium dodecyl sulphate (SDS). Polyoxyethylenesorbitan-fatty acid esters include polysorbate 20 and polysorbate 80.

A "lyoprotectant" refers to a pharmaceutically acceptable substance that stabilizes a protein during lyophilization (the process of rapid freezing and drying in a high vacuum). Examples of lyoprotectants include, without limitation, sucrose, trehalose or mannitol.

An "antioxidant" refers to a molecule capable of slowing or preventing the oxidation of other molecules. Oxidation is a chemical reaction that transfers electrons from a substance to an oxidizing agent. Oxidation reactions can produce free radicals, which start chain reactions that destabilize the protein therapeutics and ultimately affect the product activity. Antioxidants terminate these chain reactions by removing free radical intermediates, and inhibit other oxidation reactions by being oxidized themselves. As a result, antioxidants are often reducing agents, chelating agent and oxygen scavengers such as citrate, EDTA, DPTA, thiols, ascorbic acid or polyphenols. Non-limiting examples of antioxidants include ascorbic acid (AA, E300), thiosulfate, methionine, tocopherols (E306), propyl gallate (PG, E310), tertiary butylhydroquinone (TBHQ), butylated hydroxyanisole (BHA, E320) and butylated hydroxytoluene (BHT, E321).

A "preservative" is a natural or synthetic chemical that is added to products such as foods, pharmaceuticals, paints, biological samples, wood, etc. to prevent decomposition by microbial growth or by undesirable chemical changes. Preservative additives can be used alone or in conjunction with other methods of preservation. Preservatives may be antimicrobial preservatives, which inhibit the growth of bacteria and fungi, or antioxidants such as oxygen absorbers, which inhibit the oxidation of constituents. Common antimicrobial preservatives include, benzalkonium chloride, benzoic acid, cholorohexidine, glycerin, phenol, potassium sorbate, thimerosal, sulfites (sulfur dioxide, sodium bisulfate, potassium hydrogen sulfite, etc.) and disodium EDTA. Other preservatives include those commonly used in patenteral proteins such as benzyl alcohol, phenol, m-cresol, chlorobutanol or methylparaben.

The term "surfactant" as used herein means compounds that lower the surface tension (or interfacial tension) between two liquids or between a liquid and a solid. Surfactants may act as detergents, wetting agents, emulsifiers, foaming agents, and dispersants.

Examples of surfactants include polysorbate 80, fatty acid and alkyl sulfonates; benzethanium chloride, e.g., HY AMINE 1622 from Lonza, Inc. (Fairlawn, N.J.); polyoxyethylene sorbitan fatty acid esters, e.g., the TWEEN Series from Uniqema (Wilmington, Del.); and natural surfactants, such as sodium taurocholic acid, 1-palmitoyl-2-Sn-glycero-3-phosphocholine, lecithin and other phospholipids. Such surfactants, e.g., minimize aggregation of lyophilized particles during reconstitution of the product. These surfactants may comprise from about 0.001% to about 5% w/v.

II. Formulations

As provided, the wild-type fXa is a two-chain polypeptide. So are many forms of fXa antidotes, including the r-Antidote (SEQ ID NO: 3), which includes a light chain (SEQ ID NO. 4) and a heavy chain (SEQ ID NO. 5) connected with a single disulfide bond between Cysteine 98 (Cys98) of the light chain and Cysteine 108 (Cys108) of the heavy chain. Also like the wild-type fXa, the r-Antidote expressed in cells undergoes post-translational modifications resulting in glycosylation at certain amino acid residues, e.g., Ser56, Ser72, Ser76 and Thr82 of the light chain and Thr249 of the heavy chain, and a modified residue, (3R)-3-hydroxyAsp at Asp29 of the light chain. Further, in addition to the inter-chain disulfide bond, there can be one or more intra-chain disulfide bonds formed between Cysteines 16 and 27, 21 and 36, 38 and 47, 55 and 66, 62 and 75, and 77 and 90 of the light chain, and between Cysteines 7 and 12, 27 and 43, 156 and 170, and 181 and 209 of the heavy chain.

Given the two-chain structure and various post-translational modifications of the fXa antidotes, it is shown herein that development of a stable lyophilized formulation that provides a stable and soluble solution with an acceptable osmolality presents a great challenge.

Using the r-Antidote as an example, experimental data showed that a high concentration of a solubilizing agent is required to maintain a reasonable solubility for the r-Antidote. In particular, the solubility studies in Example 4 shows that both citrate and arginine significantly increase the solubility of the r-Antidote. Further, the examples showed that the r-Antidote could remain soluble in the solution when the concentration of arginine was at 95 mM, or at least 10 mM.

Further, during the lyophilization process, it was determined that the temperature of the protein needed to be maintained below the determined collapse temperature (about −40° C.) to obtain acceptable lyophilized samples (Example 6). Maintaining such low product temperature, however, is not feasible in practice. Therefore, the data demonstrate that a crystallizing component (e.g., mannitol) is required to serve as a scaffold that can hold the amorphous protein material in place during and after freeze drying.

It was further discovered, however, the presence of a high concentration of arginine (e.g., 95 mM) prevented crystallization of mannitol (Example 7). Meanwhile, the presence of mannitol increases the total concentration of sugar in the formulation, leading to unacceptable osmolality of the solution (Example 7).

Development of a suitable lyophilized formation for the r-Antidote, therefore, had conflicting requirements for the concentration of arginine as a solubilizing agent, mannitol as a crystallizing agent, and sucrose as a stabilizing agent. It was, at the best, unpredictable whether such requirements could be balanced to generate an acceptable lyophilized formation.

Surprisingly and unexpectedly, however, the present inventors were able to arrive at a solution that balances protein solubility, stability, cake structure and osmolality. More specifically, to generate a suitable lyophilized formation, an example r-Antidote solution includes about 45 mM arginine (10-55 mM), about 2% sucrose (1-3%), and about 5% mannitol (2-8%). Further, the solution includes about 10 mM tris, and 0.01%-0.02% PS80 along with a desired amount of r-Antidote (e.g., 10 mg/mL, 15 mg/mL, 20 mg/mL, 30 mg/mL, 40 mg/mL or 50 mg/mL), and has a pH of about 7.8.

Further, despite being known as a good solubilizing agent for therapeutic proteins, citrate has been shown to have anticoagulating activities. See, e.g., Wright et al., *Nephrology* (Carlton). 2011 May; 16(4):396-402. Therefore, since the r-Antidote is intended as an antidote to anticoagulating agents (fXa inhibitors), citrate was considered not suitable for use with the r-Antidote. Unexpectedly, it is discovered herein that citrate actually does not interfere with the r-Antidote's activity in vivo. A suitable concentration of citrate is found to be from about 10 mM to about 25 mM, in addition to about 2% sucrose (1-3%), and about 5% mannitol (2-8%) in a solution suitable for lyophilization.

Accordingly, when the solution is lyophilized, it will form a dry composition that includes a weight ratio of L-arginine HCl:sucrose:mannitol in the range of (0.5-1.4):(1-3):(2-8). If between 5 mg/mL and 50 mg/mL r-Antidote is used in the solution, for instance, then the weight ratio of L-arginine HCl:sucrose:mannitol:r-Antidote in the range of (0.5-1.4):(1-3):(2-8):(0.5-5).

Conversely, when such a lyophilized formulation is dissolved in water, saline, or other similar solvent, it can provide a solution that has about 10-55 mM arginine, about 1-3% sucrose, and about 2-8% mannitol.

Likewise, when a solution using citrate as the solubilizing agent is lyophilized, it will form a dry composition that includes a weight ratio of citrate:sucrose:mannitol in the range of (0.15-0.66):(1-3):(2-8). If between 5 mg/mL and 50 mg/mL r-Antidote is used in the solution, for instance, then the weight ratio of L-arginine HCl:sucrose:mannitol:r-Antidote in the range of (0.15-0.66):(1-3):(2-8):(0.5-5). Conversely, when such a lyophilized formulation is dissolved in water, saline, or other similar solvent, it can provide a solution that has about 8-35 mM citrate, about 1-3% sucrose, and about 2-8% mannitol.

The results observed with the r-Antidote can be readily extrapolated to other fXa antidotes that have similar structures including biological equivalents of r-Antidote (or their precursors, represented by SEQ ID NO: 2). In one aspect, such biological equivalents have at least 80%, 85%, 90%, or 95% sequence identity to SEQ ID NO: 3. In one aspect, such biological equivalents include two peptide chains, each having at least 80%, 85%, 90%, or 95% sequence identity to SEQ ID NO: 4 or SEQ ID NO: 5, respectively. In one aspect, such biological equivalents retain the structural characteristics of SEQ ID NO: 3, that is, a modified active site and a deleted or modified Gla domain. In another aspect, such biological equivalents retain the functional features of SEQ ID NO: 3, that is, not competing with fXa in assembling into the prothrombinase complex and having reduced or no procoagulant (e.g., enzymatic or catalytic) activities.

Also, it is contemplated that arginine can be substituted with another solubilizing agent, mannitol can be substituted with another crystallizing agent, and sucrose can be substituted with another stabilizing agent, adequate examples of each of which are available in the art and are provided in the present disclosure.

A. Polypeptide Solution Suitable for Lyophilization

In one embodiment, the present disclosure provides an aqueous formulation suitable for lyophilization, which formulation includes a fXa antidote as disclosed here or its biological equivalents, along with a solubilizing agent, a stabilizing agent (or stabilizer), and a crystalline agent. The formulation can further include a surfactant and/or a buffer. In some aspects, the presence of each of these agents prevents the fXa antidote from collapsing during lyophilization, for instance, when the freeze-dry temperature is higher than −40° C., −30° C., −20° C., −10° C., 0° C., 5° C., 10° C., or 15° C., as high as 20° C. or 25° C.

One embodiment of the disclosure provides an aqueous formulation which can be used for lyophilization. The aqueous formulation includes a fXa derivative polypeptide, e.g., a polypeptide comprising the amino acid sequence of SEQ ID NO: 3 or an amino acid sequence having at least 95% sequence identity to SEQ ID NO: 3. In addition to the polypeptide, the formulation further includes a solubilizing agent, a stabilizer, and a crystalline component. Such a formulation does not collapse during lyophilization under desired conditions. In one aspect, the desired condition is freeze drying at a temperature that is higher than −40° C., or alternatively higher than −40° C., −30° C., −20° C., −10° C., 0° C., 5° C., 10° C., or 15° C. In another aspect, the desired condition is freeze drying at a temperature that is lower than 25° C., or alternatively lower than 20° C., 15° C., 10° C., or 5° C.

In one aspect, the fXa derivative polypeptide has modifications to the Gla domain and the active site as compared to the wild-type fXa protein. In one aspect, the fXa derivative polypeptide retains fXa's ability to bind to a fXa inhibitor but does not assemble into a prothrombinase complex. In one aspect, the fXa derivative polypeptide is a two-chain polypeptide having an amino acid sequence of SEQ ID NO. 3, which includes a light chain (SEQ ID NO. 4) and a heavy chain (SEQ ID NO. 5) connected with a single disulfide bond between Cysteine 98 (Cys98) of the light chain and Cysteine 108 (Cys108) of the heavy chain. In one aspect, the aqueous formulation includes at least 5 mg/mL of the polypeptide. In one aspect, the aqueous formulation includes at least 5, 10, 15, 20, 25, 30, 35, 40, 45 or 50 mg/mL of the polypeptide.

In some aspects, a crystalline component is included in the formulation at a concentration suitable for forming a crystalline matrix during the freeze drying process. The formulation of the crystalline matrix is useful for preventing collapse, as demonstrated in the examples.

A "crystalline component" refers to a molecule that forms a crystalline matrix in a formulation that includes a polypeptide, during a freeze drying process. Non-limiting examples of crystalline components include mannitol and glycine.

In some aspects, the crystalline component is mannitol (e.g., crystalline mannitol). In one aspect, the concentration of the crystalline component in the aqueous formulation is at least 1% (w/v). In one aspect, the concentration of the crystalline component in the aqueous formulation is at least 1.5%, 2%, 2.5%, 3%, 3.5% or 4% (w/v). In one aspect, the concentration of the crystalline component in the aqueous formulation is not higher than 8%, or alternatively not higher than 7%, 6.5%, 6%, 5.5%, 5%, 4.5% or 4% (w/v). In one aspect, the concentration of the crystalline component in the aqueous formulation is from about 1% to about 8%, or from about 2% to about 6%, or from about 3% to about 5.5%, or from about 4.5% to about 5.5%, or from about 4.6% to about 5.4%, or from about 4.7% to about 5.3%, or from about 4.8% to about 5.2%, or from about 4.9% to about 5.1%, or at about 4%, 4.5%, or 5% (w/v).

In some aspects, a solubilizing agent is included in the aqueous formulation. The term "solubilizing agent" refers to salts, ions, carbohydrates, complexation agent, polymers and other compounds which, when present in solution, increases the solubility of another molecule (e.g., an active ingredient) in the solution. Non-limiting examples of solubilizing agents include arginine and citrate. In one aspect, the solubilizing agent is arginine. In one aspect, the solubilizing agent is citrate.

The presence of the solubilizing agent is demonstrated herein to be useful in keeping the fXa polypeptide soluble and stable in the formulation. In some aspects, the concentration of the solubilizing agent (e.g., arginine) is at least 10 mM, or alternatively at least 20 mM, 25 mM, 30 mM, 36 mM, or 40 mM. In some aspects, the concentration of the solubilizing agent (e.g., arginine) is not higher than 100 mM, 96 mM, 90 mM, 80 mM, 70 mM, 60 mM or 50 mM. In some aspects, the concentration of the solubilizing agent is from about 10 mM or 20 mM to about 60 mM, from about 10 mM or 20 mM to about 55 mM, from about 35 mM to about 55 mM, from about 40 mM to about 50 mM, from about 41 mM to about 49 mM, from about 42 mM to about 48 mM, from about 43 mM to about 47 mM, from about 44 mM to about 46 mM, or at about 40 mM, 45 mM or 50 mM. It is noted that as used herein, the term arginine refers to the amino acid as well as the salts (e.g., arginine HCl) thereof. Arginine has a molecular weight of about 174.2 Dalton and arginine HCl (e.g., L-arginine HCl) has a molecular weight of about 210.7 Dalton.

In one embodiment, the solubilizing agent is citrate or a salt thereof. The salt of citrate is sodium citrate. In one aspect, the citrate comprises a concentration from about 1.0 mM to about 200.0 mM. In a further aspect, the concentration of the citrate is about 25 mM. In another aspect, the concentration of the citrate is about 50 mM. In further embodiment, the concentration of the citrate is about 5 mM, 10 mM, or 20 mM. In another embodiment, the citrate comprises a concentration from about 0.05 M to about 0.2 M.

In some aspects, a stabilizer is included in the aqueous formulation. The term "stabilizer" denotes a pharmaceutical acceptable excipient, which protects the active ingredient (e.g., the fXa derivative polypeptides) and/or the formulation from chemical and/or physical degradation during manufacturing, storage and application. Examples of stabilizers may be include sucrose, arginine, citrate, mannitol, trehalose, glycine, sodium chloride, dextran and glucose. In one aspect, the stabilizer is sucrose.

In one aspect, the concentration of the stabilizer in the aqueous formulation (e.g., sucrose) is at least about 0.5% (w/v). In one aspect, the concentration of the stabilizer in the aqueous formulation (e.g., sucrose) is at least about 0.6%, 0.7%, 0.8%, 0.9%, 1%, 1.1%, 1.2%, 1.3%, 1.4%, 1.5%, 1.6%, 1.7%, 1.8%, 1.9% or 2% (w/v). In one aspect, the concentration of the stabilizer in the aqueous formulation (e.g., sucrose) is not greater than about 5%, 4.5%, 4%, 3.5%, 3%, 2.5% or 2% (w/v). In one aspect, the concentration of the stabilizer in the aqueous formulation (e.g., sucrose) is from about 1% to about 5%, or from about 1% to about 4%, or from about 1% to about 3%, or from about 1.5% to about 2.5%, or from about 1.6% to about 2.4%, or from about 1.7% to about 2.3%, or from about 1.7% to about 2.2%, or from about 1.9% to about 2.1%, or at about 1%, 1.5%, 2%, 2.5% or 3% (w/v).

In some aspects, the aqueous formulation can further include a surfactant, a buffer, a tonicity agent, a cryoprotectant, a surfactant, a lyoprotectant, a preservative or combinations thereof.

In some aspects, the aqueous formulation has a pH that is 6 or higher, or 6.5 or higher, or 7 or higher, or 7.5 or higher. In some aspects, the pH is not higher than 9, 8.5, or 8. In some aspects, the pH is between 6 and 9, between 6.5 and 8.5, between 7 and 8.5, between 7.5 and 8.2, between 7.6 and 8.1, between 7.7 and 7.9, or at about 7.5, 7.6, 7.7, 7.8, 7.9 or 8.

In one aspect, the aqueous formulation includes about 45 mM arginine, about 2% sucrose (w/v), about 5% mannitol (w/v) and about 10 mg/mL of a two-chain r-Antidote, wherein the formulation has a pH of about 7.8. In one aspect, the aqueous formulation includes about 45 mM arginine, about 2% sucrose (w/v), about 5% mannitol (w/v) and about 20 mg/mL of a two-chain r-Antidote, wherein the formulation has a pH of about 7.8. In one aspect, the aqueous formulation includes about 45 mM arginine, about 2% sucrose (w/v), about 5% mannitol (w/v) and about 40 mg/mL of a two-chain r-Antidote, wherein the formulation has a pH of about 7.8. In one aspect, the aqueous formulation further includes 0.01%-0.02% (w/v) Polysorbate 80 and a buffer.

B. Lyophilization and Lyophilized Compositions

Also provided, in some embodiments, are methods of lyophilizing the aqueous formulations of the present disclosure. In one aspect, the disclosure provides a conservative lyophilization cycle as exemplified in Table 8.2, which includes a freezing step, an isothermal step, an annealing step, a primary drying step and a secondary drying step.

In another aspect, the lyophilization cycle includes the steps as described in Table 6. It is further noted that, once an aqueous solution suitable for lyophilization is identified, the method of lyophilizing the solution can be derived accordingly, with methods known in the art. In one aspect, one, or more or all of the drying steps are carried out at a temperature of −40° C. or higher. In one aspect, the drying steps are carried out at a temperature of −35° C., −30° C., −25° C., −20° C., −10° C. or 0° C. or higher, but not higher than 10° C., 15° C., 20° C. or 25° C.

In some aspects, also provided are lyophilized compositions prepared by lyophilizing the aqueous formulation of the present disclosure. Based on the concentrations of each agent in the aqueous formulation, the relative content of the agent in the lyophilized composition can readily be determined.

In one aspect, the lyophilized composition includes at least 5%, or alternatively at least 10%, 15%, 20%, 25%, 30%, or 35% (w/w) of the fXa derivative polypeptide. Then, among the other main ingredients, for instance, there can be a weight ratio for L-arginine HCl:sucrose:mannitol in the range of (0.5-1.4):(1-3):(2-6). In some aspects, the weight ratio of L-arginine HCl:sucrose:mannitol is in the range of (0.9-1):(1.5-2.5):(4.5-5.5), or (0.91-0.99):(1.6-2.4):(4.6-5.4), or (0.92-0.98):(1.7-2.3):(4.7-5.3), (0.93-0.97):(1.8-2.2):(4.8-5.2), or (0.94-0.96):(1.9-2.1):(4.9-5.1). In some aspects, the lyophilized composition further includes a surfactant and/or the solid portion of a buffer.

Still, in some aspects, provided is a solution prepared by dissolving the lyophilized composition of the present disclosure in a solvent. In some aspects, the solvent is water or saline. In one aspect, the solvent is water. In one aspect, the solution includes at least 5 mg/ml or alternatively at least 10 mg/ml of the target polypeptide.

In one embodiment, the present disclosure provides a lyophilized composition comprising at least 10% (w/w) of the r-Antidote, and L-arginine HCl:sucrose:mannitol in a weight ratio of about 0.95:2:5. In one embodiment, the present disclosure provides a lyophilized composition comprising at least 20% (w/w) of the r-Antidote, and L-arginine HCl:sucrose:mannitol in a weight ratio of about 0.95:2:5. In one embodiment, the present disclosure provides a lyophilized composition comprising at least 40% (w/w) of the r-Antidote, and L-arginine HCl:sucrose:mannitol in a weight ratio of about 0.95:2:5.

III. Methods of Using the Formulations

The present disclosure also relates to therapeutic methods of treating, preventing or reducing bleeding in a subject undergoing anticoagulant therapy with a fXa inhibitor comprising administering to a subject an effective amount of the lyophilized formulation upon being dissolved in a suitable solvent. It is contemplated that the antidotes or derivatives of the present disclosure may be short-duration drugs to be used in elective or emergency situations, which can safely and specifically neutralize a fXa inhibitor's conventional anticoagulant properties without causing deleterious hemodynamic side-effects or exacerbation of the proliferative vascular response to injury.

As used herein, the terms "treating," "treatment" and the like are used herein to mean obtaining a desired pharmacologic and/or physiologic effect. The effect may be prophylactic in terms of completely or partially preventing a disorder or sign or symptom thereof, and/or may be therapeutic in terms of a partial or complete cure for a disorder and/or adverse effect attributable to the disorder.

"Treating" also covers any treatment of a disorder in a mammal, and includes: (a) preventing a disorder from occurring in a subject that may be predisposed to a disorder, but may have not yet been diagnosed as having it, e.g., prevent bleeding in a patient with anticoagulant overdose; (b) inhibiting a disorder, i.e., arresting its development, e.g., inhibiting bleeding; or (c) relieving or ameliorating the disorder, e.g., reducing bleeding.

As used herein, to "treat" further includes systemic amelioration of the symptoms associated with the pathology and/or a delay in onset of symptoms. Clinical and subclinical evidence of "treatment" will vary with the pathology, the individual and the treatment.

"Administration" can be effected in one dose, continuously or intermittently throughout the course of treatment. Methods of determining the most effective means and dosage of administration are known to those of skill in the art and will vary with the composition used for therapy, the purpose of the therapy, the target cell being treated, and the subject being treated. Single or multiple administrations can be carried out with the dose level and pattern being selected by the treating physician. Suitable dosage formulations and methods of administering the agents are known in the art. A "subject" of diagnosis or treatment is a cell or a mammal, including a human. Non-human animals subject to diagnosis or treatment include, for example, murine, such as rats, mice, canine, such as dogs, leporids, such as rabbits, livestock, sport animals, and pets.

The agents and compositions of the present disclosure can be used in the manufacture of medicaments and for the treatment of humans and other animals by administration in accordance with conventional procedures, such as an active ingredient in pharmaceutical compositions.

An agent of the present disclosure can be administered for therapy by any suitable route, specifically by parental (including subcutaneous, intramuscular, intravenous and intradermal) administration. It will also be appreciated that the preferred route will vary with the condition and age of the recipient, and the disease being treated.

The phrase "pharmaceutically acceptable polymer" refers to the group of compounds which can be conjugated to one or more polypeptides described here. It is contemplated that the conjugation of a polymer to the polypeptide is capable of extending the half-life of the polypeptide in vivo and in vitro. Non-limiting examples include polyethylene glycols, polyvinylpyrrolidones, polyvinylalcohols, cellulose derivatives, polyacrylates, polymethacrylates, sugars, polyols and mixtures thereof.

"Anticoagulant agents" or "anticoagulants" are agents that inhibit blood clot formation. Examples of anticoagulant agents include, but are not limited to, specific inhibitors of thrombin, factor IXa, factor Xa, factor XIa, factor XIIa or factor VIIa, heparin and derivatives, vitamin K antagonists, and anti-tissue factor antibodies. Examples of specific inhibitors of thrombin include hirudin, bivalirudin (Angiomax®), argatroban and lepirudin (Refludan®). Examples of heparin and derivatives include unfractionated heparin (UFH), low molecular weight heparin (LMWH), such as enoxaparin (Lovenox®), dalteparin (Fragmin®), and danaparoid (Orgaran®); and synthetic pentasaccharide, such as fondaparinux (Arixtra®). Examples of vitamin K antagonists include warfarin (Coumadin®), phenocoumarol, acenocoumarol (Sintrom®), clorindione, dicumarol, diphenadione, ethyl biscoumacetate, phenprocoumon, phenindione, and tioclomarol. In one embodiment, the anticoagulant is an inhibitor of factor Xa. In one embodiment, the anticoagulant is betrixaban.

"Anticoagulant therapy" refers to a therapeutic regime that is administered to a patient to prevent undesired blood clots or thrombosis. An anticoagulant therapy comprises administering one or a combination of two or more anticoagulant agents or other agents at a dosage and schedule suitable for treating or preventing the undesired blood clots or thrombosis in the patient.

The term "factor Xa inhibitors" or "inhibitors of factor Xa" refer to compounds that can inhibit, either directly or indirectly, the coagulation factor Xa's activity of catalyzing conversion of prothrombin to thrombin in vitro and/or in vivo.

"Direct factor Xa inhibitors" bind to the fXa directly and non-limiting examples include NAP-5, rNAPc2, tissue factor pathway inhibitor (TFPI), DX-DX-9065a (as described in, e.g., Herbert, J. M., et al, *J Pharmacol Exp Ther.* 1996 276(3):1030-8), YM-60828 (as described in, e.g., Taniuchi, Y., et al, *Thromb Haemost.* 1998 79(3):543-8), YM-150 (as described in, e.g., Eriksson, B. I. et. al, *Blood* 2005; 106(11), Abstract 1865), apixaban, rivaroxaban, TAK-442, PD-348292 (as described in, e.g., Pipeline Insight: Antithrombotics—Reaching the Untreated Prophylaxis Market, 2007), otamixaban, edoxaban (as described in, e.g., Hylek E M, Curr Opin Invest Drugs 2007 8(9):778-783), LY517717 (as described in, e.g., Agnelli, G., et al, *J. Thromb. Haemost.* 2007 5(4):746-53), GSK913893, razaxaban, betrixaban or a pharmaceutically acceptable salt thereof, and combinations thereof. In a particular aspect, the direct factor Xa inhibitor is rivaroxaban. In some aspects, a direct fXa inhibitor is a small molecule chemical compound.

"Indirect factor Xa inhibitors" inhibition of the fXa activity is mediated by one or more other factors. Non-limiting examples of indirect factor Xa inhibitors include fondaparinux, idraparinux, biotinylated idraparinux, enoxaparin, fragmin, tinzaparin, low molecular weight heparin ("LMWH"), and combinations thereof. In a particular aspect, the indirect factor Xa inhibitor is enoxaparin.

In one embodiment, the factor Xa inhibitor is selected from betrixaban, rivaroxaban, LMWH, DX-9065a, YM-60828, YM-150, PD-348292, otamixaban, edoxaban, LY517717, GSK913893, razaxaban, apixaban, and combinations thereof.

The term "betrixaban" refers to the compound "[2-({4-[(dimethylamino)iminomethyl]phenyl}carbonylamino)-5-methoxyphenyl]-N-(5-chloro(2-pyridyl))carboxamide" or pharmaceutically acceptable salts thereof. "[2-({4-[(dimethylamino)iminomethyl]phenyl}carbonylamino)-5-methoxyphenyl]-N-(5-chloro(2-pyridyl))carboxamide" refers to the compound having the following structure:

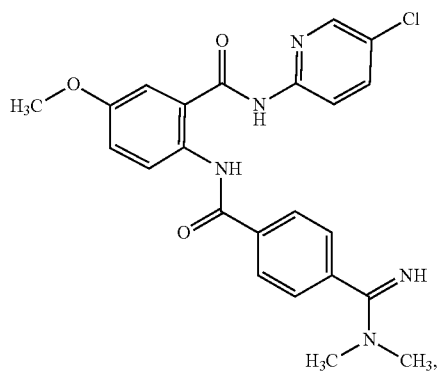 [SMILES: COc1ccc(NC(=O)c2ccc(C(=N)N(C)C)cc2)c(C(=O)Nc2ccc(Cl)cn2)c1]

or a tautomer or pharmaceutically acceptable salt thereof.

Betrixaban is described in U.S. Pat. Nos. 6,376,515 and 6,835,739 and U.S. Patent Application Publication No. 2007/0112039, filed on Nov. 7, 2006, the contents of which are incorporated herein by reference. Betrixaban is known to be a specific inhibitor of factor Xa.

"Neutralize," "reverse" or "counteract" the activity of an inhibitor of fXa or similar phrases refer to inhibit or block the factor Xa inhibitory or anticoagulant function of a fXa inhibitor. Such phrases refer to partial inhibition or blocking of the function, as well as to inhibiting or blocking most or all of fXa inhibitor activity, in vitro and/or in vivo.

"An effective amount" refers to the amount of derivative sufficient to induce a desired biological and/or therapeutic result. That result can be alleviation of the signs, symptoms, or causes of a disease, or any other desired alteration of a biological system. In the present disclosure, the result will typically involve one or more of the following: neutralization of a fXa inhibitor that has been administered to a patient, reversal of the anticoagulant activity of the fXa inhibitor, removal of the fXa inhibitor from the plasma, restoration of hemostasis, and reduction or cessation of bleeding. The effective amount will vary depending upon the specific antidote agent used, the specific fXa inhibitor the subject has been administered, the dosing regimen of the fXa inhibitor, timing of administration of the antidote, the subject and disease condition being treated, the weight and age of the subject, the severity of the disease condition, the manner of administration and the like, all of which can be determined readily by one of ordinary skill in the art.

In certain aspects, the solution is administered to deliver an amount of the fXa derivative (e.g., the r-antidote) from about 10 milligrams (mg) to about 2 grams (g). Other amounts of the r-antidote used include from about 100 mg to about 1.5 g; from about 200 mg to about 1 g; and from about 400 mg to about 900 mg. In some aspects, the amount of the r-antidote used is about 400 mg or 960 mg. In some aspects, the amount of the r-antidote used is from about 10 mg to about 100 mg; from about 15 mg to about 95 mg; and from about 20 mg to about 80 mg.

In another embodiment, the solution administered in a neutralizing amount that is at least about a 1:1 fold molar ratio of circulating concentration of r-antidote over circulating concentration of the factor Xa inhibitor for a period of at least about 30 minutes. In other embodiments the molar ratio is about 1:1 or about 2:1 or about 4:1.

The formulation when administered neutralizes the factor Xa inhibitor by at least about 20%, or by at least about 50%, or by at least about 75%, or by at least about 90%, or by at least about 95%.

One can determine if the method, i.e., inhibition or reversal of a factor Xa inhibitor is achieved, by a number of in vitro assays, such as thrombin generation assay, and clinical clotting assays such as aPTT, PT and ACT.

One aspect of the present disclosure relates methods of selectively binding and inhibiting an exogenously administered fXa inhibitor in a subject undergoing anticoagulant therapy with a fXa inhibitor comprising administering to the subject an effective amount of a solution of the lyophilized formulation. Patients suitable for this therapy have undergone prior anticoagulant therapy, for example, they have been administered one, or more of an anticoagulant, such as a direct or indirect inhibitor of fXa.

In some embodiments, the solution is administered after the administration of an overdose of a fXa inhibitor or prior to a surgery, which may expose subjects to the risk of hemorrhage. The subject may be a cell or a mammal, such as a human.

In another aspect the method provide herein selectively binds and inhibits an exogenously administered factor Xa inhibitor in a subject undergoing anticoagulant therapy with a factor Xa inhibitor comprising administering a solution of the lyophilized formulation to the subject. The subject may be a cell or a mammal, such as a human.

Subjects that will benefit from the administration of the dissolved lyophilized formulation described herein and the accompanying methods include those that are experiencing, or predisposed to a clinical major bleeding event or a clinically significant non-major bleeding event. Examples of clinical major bleeding events are selected from the group consisting of hemorrhage, bleeding into vital organs, bleeding requiring re-operation or a new therapeutic procedure, and a bleeding index of ≥2.0 with an associated overt bleed. (Turpie A G G, et al, *NEJM,* 2001, 344: 619-625.) Additionally, the subject may be experiencing or predisposed to a non-major bleeding event selected from the group consisting of epistaxis that is persistent or recurrent and in substantial amount or will not stop without intervention, rectal or urinary tract bleeding that does not rise to a level requiring a therapeutic procedure, substantial hematomas at injection sites or elsewhere that are spontaneous or occur with trivial trauma, substantial blood loss more than usually associated with a surgical procedure that does not require drainage, and bleeding requiring unplanned transfusion.

In some embodiments, the dissolved lyophilized formulation is administered after the administration of an overdose of a fXa inhibitor or prior to a surgery, which may expose subjects to the risk of hemorrhage.

In any of the methods described herein, it should be understood, even if not always explicitly stated, that an effective amount of the dissolved lyophilized formulation is administered to the subject. The amount can be empirically determined by the treating physician and will vary with the age, gender, weight and health of the subject. Additional factors to be considered by the treating physician include but are not limited to the identity and/or amount of factor Xa inhibitor, which may have been administered, the method or mode that the lyophilized formulation will be administered to the subject, and the therapeutic end point for the patient. With these variables in mind, one of skill will administer a therapeutically effective amount to the subject to be treated.

EXAMPLES

The disclosure is further understood by reference to the following examples, which are intended to be purely exemplary of the disclosure. The present disclosure is not limited in scope by the exemplified embodiments, which are intended as illustrations of single aspects of the disclosure only. Any methods that are functionally equivalent are within the scope of the disclosure. Various modifications of the disclosure in addition to those described herein will become apparent to those skilled in the art from the foregoing description and accompanying figures. Such modifications fall within the scope of the appended claims.

Unless otherwise stated all temperatures are in degrees Celsius. Also, in these examples and elsewhere, abbreviations have the following meanings:

hr=hour
INR=international normalized ratio
IV=intravenous
kg=kilogram
M=molar
mg=milligram
mg/kg=milligram/kilogram
mg/mL=milligram/milliliter
min=minute
mL=milliliter
PPP=platelet poor plasma
PRP=platelet rich plasma
PT=prothrombin time
U/mL=units/milliliter
μL or uL=microliter
μM=Micromolar

Example 1. Preparation of r-Antidote

Citrate-phosphate (20 mM) buffers with an ionic strength of 0.15 (adjusted with NaCl) were prepared using citric acid monohydrate (Fisher, Pittsburgh, Pa.) and sodium phosphate dibasic, anhydrous (Sigma, St. Louis, Mo.) and the pH was adjusted using either 6 M HCl or 6 M NaOH. Phosphate (20 mM) buffer without additional salt was prepared by dissolving 6.61 g of sodium phosphate dibasic anhydrous in 2.0 L of Mili-Q water and pH adjusted to 7.5. For the phosphate (20 mM) buffer containing salt (I=0.15 M), 14.8 g NaCl was added to the phosphate buffer described above. All other reagents were purchased from Sigma (St. Louis, Mo.) unless otherwise noted.

The polypeptide of the r-Antidote (SEQ ID NO. 3) was stored in stock solution of a concentration of approximately 5 mg/ml in 10 mM Tris, pH 8.0 containing 2% arginine. The dialysis of the r-Antidote was performed at 4° C. using Slide-A-Lyzer® Dialysis Cassettes, 3000 MWCO (Pierce, Rockford, Ill.) against citrate-phosphate buffers of selected pH values. To prevent aggregation during dialysis, the stock protein solution was diluted to 0.5 mg/ml with filtered dialysis buffer prior to loading into cassettes. After dialysis, the r-Antidote was diluted to 0.3 mg/ml and protein concentration was measured with UV absorbance spectroscopy ($A_{280}$) using an extinction coefficient of 1.16 ml·mg$^{-1}$·cm$^{-1}$. The r-Antidote produced by this method was used in the following examples.

Example 2. Differential Scanning Calorimetry (DSC) for Stability Monitoring

Differential Scanning Calorimetry (DSC) was performed using a Microcal capillary auto-DSC with a temperature controlled sample loading chamber. Thermal ramps were performed from 6-100° C. with a scanning rate of 60° C./hr and a 25 minute pre-scanning equilibration period. Appropriate matching buffer was used in the reference cell, while typical sample concentrations in matching buffer were ~0.6 mg/mL. A buffer versus buffer reference scan was subtracted from all sample scans and the thermograms were concentration normalized prior to analysis. Data were processed using the supplied software from Microcal. Endothermic peaks were fit to a single peak using a non two-state fitting function, and transition temperature (Tm) values were calculated by the fitting function. The onset temperatures (Tonset) values were determined by the deviation of the endothermic peak from a low temperature baseline.

DLS is often employed to show the presence of multiple populations in a heterogeneous sample. Using a Wyatt plate reader DLS instrument, 10-20 μL of protein solution (0.3 mg/mL) at different pH conditions was measured in a single set of experiments at 20° C. The samples were centrifuged for 5 min at 3000 rpm to remove any air bubbles, and 5 scans of 20 seconds each were acquired to give an average sample radius. At pH 5.0-7.5, a single population with a hydrodynamic radii~3 nm were observed.

Example 3. Identification of Stabilizers

Data from Example 2 demonstrated that the r-Antidote was overall stable at pH 7.5. Thus, the excipient screening studies were performed at pH 7.5 in a 20 mM phosphate buffer. The hydrodynamic diameter of the protein was measured using a Dynapro dynamic light scattering plate reader instrument (Wyatt Technology, Santa Barbara, Calif.). The hydrodynamic diameter was calculated from the diffusion coefficient by the Stokes-Einstein equation using the method of cumulants (lognormal number based). The measurements were used to evaluate the homogeneity of the supplied sample.

A SpectraMax M3 plate reader was first employed to identify potential stabilizing excipients by monitoring the protein aggregation kinetics at 60° C., pH 7.5 with 0.3 mg/ml protein with or without excipients. In total, 32 excipients from a library of Generally-Regarded-As-Safe (GRAS) excipients were tested as listed in Table 4.1.

TABLE 4.1

Excipient List and Concentrations Tested by OD 350 nm Kinetics Study

| Excipient | Concentration | Excipient | Concentration |
|---|---|---|---|
| Dextran Sulfate | 0.0075 mM | Tween 20 ™ Polysorbate 20 | 0.10% |
| Dextran T70 | 0.0075 mM | Tween 80 ™ Polysorbate 80 | 0.10% |
| Ascorbic acid | 0.15M | Pluronic F-68 | 0.10% |
| Aspartic Acid | 0.15M | Albumin | 5.00% |
| GlutamicAcid | 0.15M | Gelatin | 5.00% |
| Lactic Acid | 0.15M | Lactose | 20.0% |
| Malic Acid | 0.15M | Trehalose | 10.00% |
| Arginine | 0.3M | Dextrose | 20.00% |
| Diethanolamine | 0.3M | Sucrose | 20.0% |
| Guanidine | 0.3M | Mannitol | 10.00% |
| Lysine | 0.3M | Sorbitol | 20.00% |
| Proline | 0.3M | Glycerol | 20.00% |
| Glycine | 0.3M | α Cyclodextrin | 2.50% |
| Calcium Chloride | 0.015M | 2-OH propyl β-CD | 10.00% |
| Sodium Citrate | 0.2M | 2-OH propyl γ-CD | 10.00% |
| Brij 35 | 0.10% | EDTA | 1 mM & 5 mM |

It was determined that of the excipients tested, sucrose, sorbitol and citrate had the largest stabilization effect. The subsequent testing of the effect of excipient combinations on protein stability were based on these three excipients as summarized in Table 4.2. The OD 350 nm melts were run in duplicate and the ΔT values for each formulation were calculated as described above. Based on ΔT values shown in Table 2, formulations 3, 4, 5 and 6 were identified to have the greatest stabilizing effect.

TABLE 4.2

List of Excipient Combinations Tested and the Corresponding ΔT Values and Solution Osmolality.

| No. | Components | ΔT (° C.) | Osmolality (mOsm/kg) |
|---|---|---|---|
| 1 | Sucrose 10% + Sorbitol 5% | 3.1 | 943 ± 13 |
| 2 | Sucrose 5% + Sorbitol 10% | 3.8 | 1066 ± 8 |
| 3 | Sucrose 10% + Sorbitol 5% + Sodium Citrate 0.05M | >10.0 | 1098 ± 21 |
| 4 | Sucrose 5% + Sorbitol 10% + Sodium Citrate 0.05M | >10.0 | 1253 ± 8 |
| 5 | Sucrose 5% + Sorbitol 5% + Sodium Citrate 0.05M | 6.2 | 863 ± 10 |
| 6 | Sucrose 10% + Sodium Citrate 0.05M | 6.5 | 755 ± 9 |
| 7 | Sorbitol 10% + Sodium Citrate 0.05M | 5.8 | 1008 ± 6 |

The ΔT is the difference between transition temperatures of protein alone and protein with different combination of excipients at pH 7.5. The osmolality is averaged from triplicate measurements and ΔT is averaged from duplicate measurements.

The aggregation properties of the therapeutic protein in these formulations were further studied using the OD 350 nm melt method in 20 mM phosphate buffer at pH 7.5, without NaCl, in these combination formulations. In general, the extent of aggregation is much lower without NaCl. In fact, the OD 350 nm melt was initially run from 35-75° C., and since no obvious aggregation was observed, the melt experiments were re-run with the same samples from 75 to 100° C. Thus, a break can be observed in the OD 350 nm curve at 75° C. due to ~10 min dwell at this temperature. No obvious aggregation was observed for proteins in formulations 3, 4, 5 and 6 even after ramping up to 100° C. Another benefit of removing additional NaCl is that the corresponding osmolality of the formulations is much lower compared to those formulations with NaCl.

Example 4. Solubility Testing

This example tests the effect of pH, temperature, stabilizers (e.g., citrate, arginine, glycine, and lysine) and ionic strength on the solubility of the r-Antidote.

Material & Methods

The material used was a solution of r-Antidote (4.8 mg/ml) in 10 mM Tris pH8.0, and 2% arginine. For solubility at room temperature (RT), testing was conducted by physical observation for at least 1-2 hrs. For solubility at 5° C., samples were equilibrated at 5° C. overnight and physical observation was conducted on the samples. In addition, the samples were centrifuged at 5° C. for 15 min and protein concentrations in supernatant were analyzed by UV A280 nm (duplicate dilution). The original stock solution was analyzed daily as control.

When protein precipitation was observed, the solubility determined from supernatant concentration was interpreted as <XX mg/mL (shaded bars in the corresponding figures). This is due to excess amount of protein presence and preferential precipitation of a sub-population of protein that has PI close to the buffer pH. When protein precipitation is not observed, the solubility determined from solution concentration was interpreted as >XX mg/mL (empty bars in the figures).

Impact of pH on solubility at room temperature was tested with different pH, including 5.0, 6.0, 7.0 and 8.0. As shown in FIG. 1A, the r-Antidote had the highest solubility at pH 8.0 (42.2 mg/mL with no visible precipitation). By contrast, the solubility was 3.5 mg/mL (no precipitation), 12.3 mg/mL (precipitation observed) and 24.4 mg/mL (precipitation observed) at pH 5.0, 6.0 and 7.0, respectively.

Table 5.1 lists samples tested for the solubility at 5° C. As shown, the UF buffer is composed of 42 mM MES, 4 mM Sodium Phosphate, 833 mM NaCl, 8 mM Tris, and 58 mM arginine concentrated to ~5 mg/mL.

TABLE 5.1

Samples tested for r-Antidote solubility at different pH with different solubilizers (citrate or arginine)

| Sample | Composition | Citrate/Arginine | pH (±0.02) | Calculated Osmolality |
|---|---|---|---|---|
| 10 mM Citrate | 10 mM Na phos, 9.5% sucrose, 0.01% PS80, 10 mM Citrate | 10 mM Citrate | 7.30 | 353 |
| 3 mM Citrate | 10 mM Na phos, 9.5% sucrose, 0.01% PS80, 3 mM Citrate | 3 mM Citrate | 7.30 | 325 |
| 0 mM Citrate | 10 mM Na phos, 9.5% sucrose, 0.01% PS80 | 0 mM Citrate | 7.30 | 313 |
| pH 7.80 | 10 mM Na phos, 9.5% sucrose, 0.01% PS80 | n/a | 7.80 | 313 |
| pH 7.55 | 10 mM Na phos, 9.5% sucrose, 0.01% PS80 | n/a | 7.55 | 313 |
| UF buffer | 42 mM MES, 4 mM NaPhos. 833 mM NaCl, 8 mM Tris, 58 mM Arg | 58 mM Arg | 7.48 | 1942 |

Figure 1B:
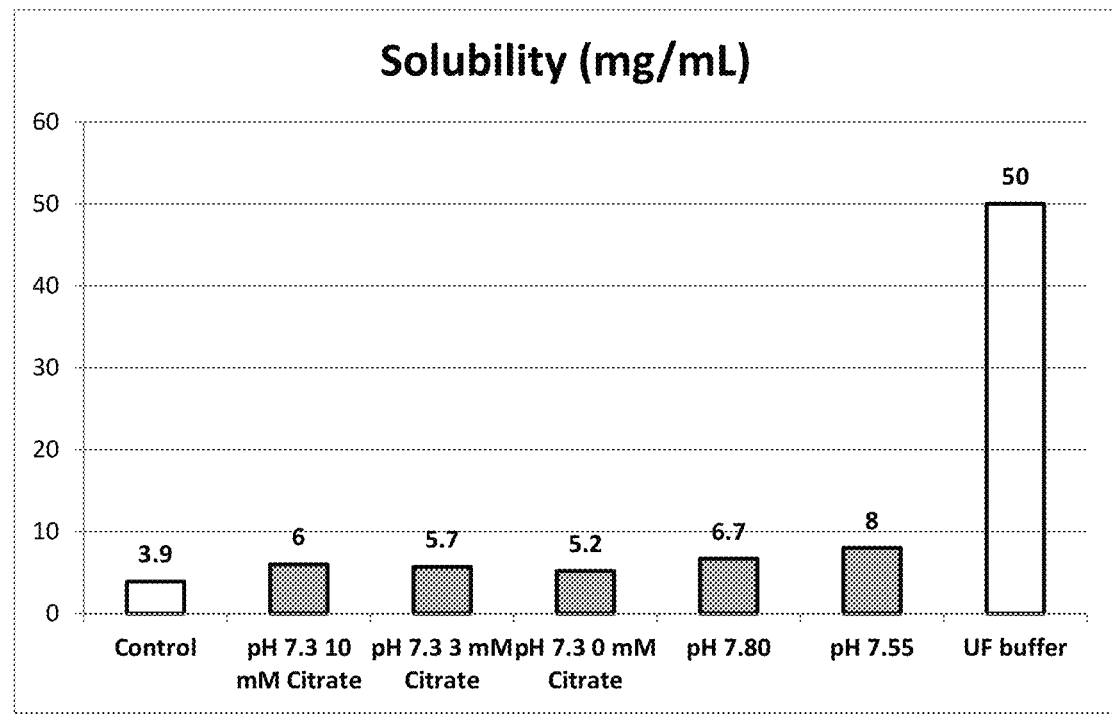

At pH 7.3, 10 mM citrate improved antidote 5° C. solubility slightly. Without citrate or arginine, 5° C. solubility had following rank order: pH 7.55>pH 7.80>pH 7.30 (FIG. 1B). The UF buffer (pH 7.48) appeared to have best solubility (50 mg/mL), likely due to presence of 58 mM Arg+833 mM NaCl at the suitable pH, 7.5 (FIG. 1B).

Figure 1C:
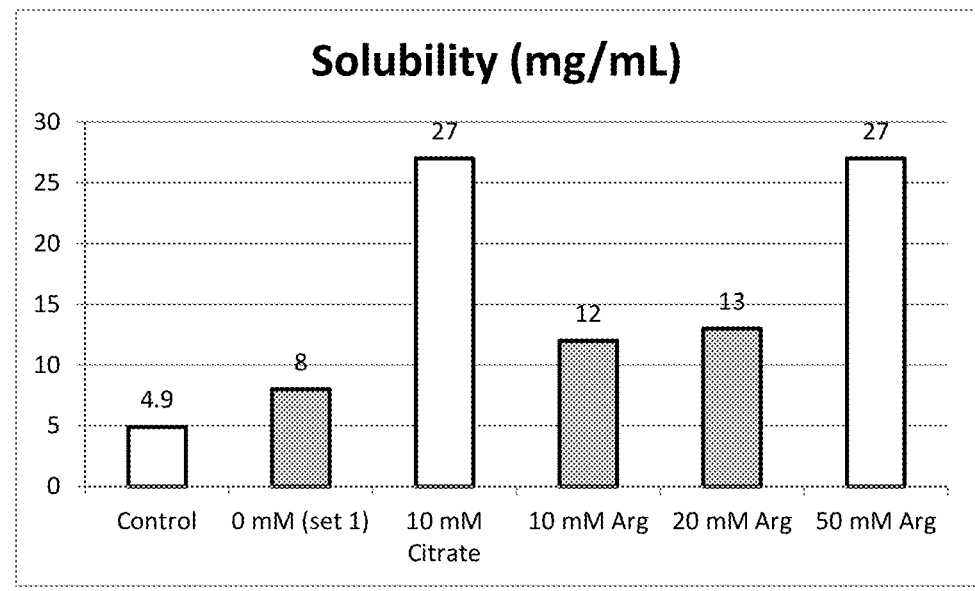

Table 5.2 lists samples for testing the effect of arginine versus citrate at pH 7.55. As shown in FIG. 1C, at pH 7.55, both citrate and arginine improved r-Antidote 5° C. solubility significantly. Further, it appeared that Citrate was more effective than arginine at the same molarity: ~10 mM citrate~50 mM arginine>20 mM arginine>10 mM arginine.

TABLE 5.2

Samples tested for r-Antidote solubility in citrate and arginine at pH 7.55

| Sample | Composition | Citrate/Arg | pH (±0.02) | Cacl Osm |
|---|---|---|---|---|
| 0 mM | 10 mM Na phos, 9.5% sucrose, 0.01% PS80 (set 1) | n/a | 7.55 | 313 |
| 10 mM Citrate | 10 mM Na phos, 8% sucrose, 0.01% PS80, 10 mM Citrate | 10 mM Citrate | 7.55 | 307 |
| 10 mM Arg | 10 mM Na phos, 8% sucrose, 0.01% PS80, 10 mM Arg | 10 mM Arg | 7.55 | 297 |
| 20 mM Arg | 10 mM Na phos, 8% sucrose, 0.01% PS80, 20 mM Arg | 20 mM Arg | 7.55 | 327 |
| 50 mM Arg | 10 mM Na phos, 8% sucrose, 0.01% PS80, 50 mM Arg | 50 mM Arg | 7.55 | 417 |

Figure 1D:
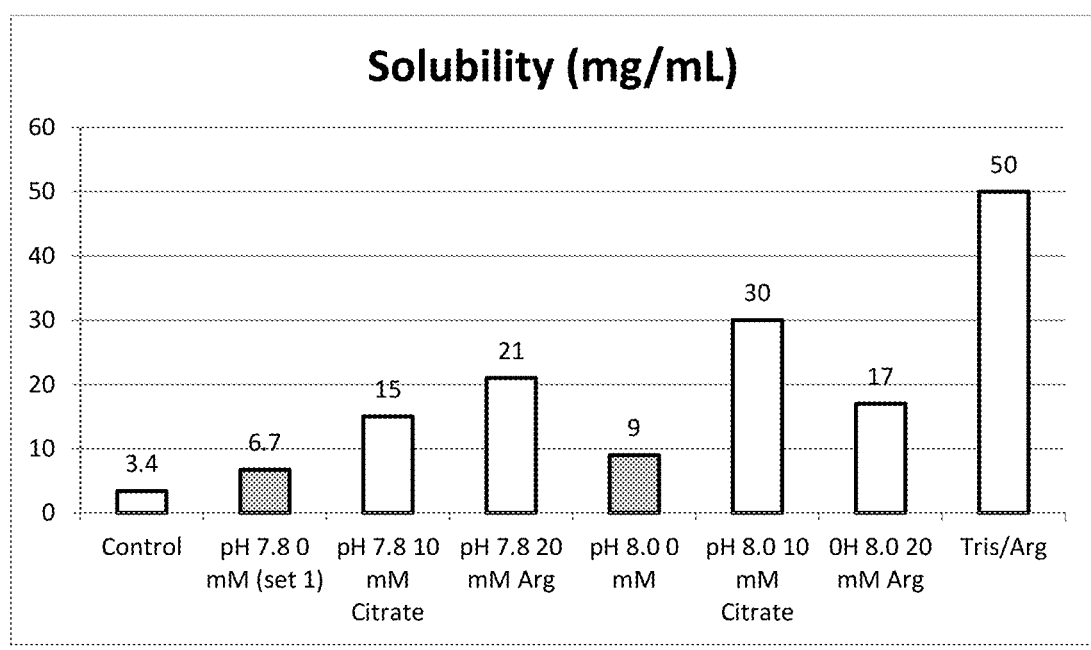

The effect of arginine versus citrate was further tested at pH 7.8 and 8.0, using the samples in Table 5.3. FIG. 1D shows that the r-Antidote was slightly more soluble at pH 8.0 than at pH 7.8 at 5° C. Both 10 mM Citrate and 20 mM Argnine improved solubility to at least 15 mg/mL at pH 7.8 and 8.0.

TABLE 5.3

Samples tested for r-Antidote solubility in citrate and arginine at pH 7.8 and 8

| Sample | Base Composition | Additional Citrate/Arg | pH (±0.02) | Cacl Osm |
|---|---|---|---|---|
| pH 7.8 | 10 mM Na phos, 9.5% sucrose, 0.01% PS80 (set 1) | n/a | 7.80 | 313 |
| pH 7.8, 10 mM Citrate | 10 mM Na phos, 8% sucrose, 0.01% PS80, 10 mM Citrate | 10 mM Citrate | 7.80 | 307 |
| pH 7.8, 20 mM Arg | 10 mM Na phos, 8% sucrose, 0.01% PS80, 20 mM Arg | 20 mM Arg | 7.80 | 327 |
| pH 8.0 | 10 mM Na phos, 8% sucrose, 0.01% PS80 | n/a | 8.00 | 267 |
| pH 8.0, 10 mM Citrate | 10 mM Na phos, 8% sucrose, 0.01% PS80, 10 mM Citrate | 10 mM Citrate | 8.00 | 307 |
| pH 8.0, 20 mM Arg | 10 mM Na phos, 8% sucrose, 0.01% PS80, 20 mM Arg | 20 mM Arg | 8.00 | 327 |
| Tris/Arg | 10 mM Tris, 2% Arg | 114 mM Arg | 8.00 | 352 |

Figure 1E:
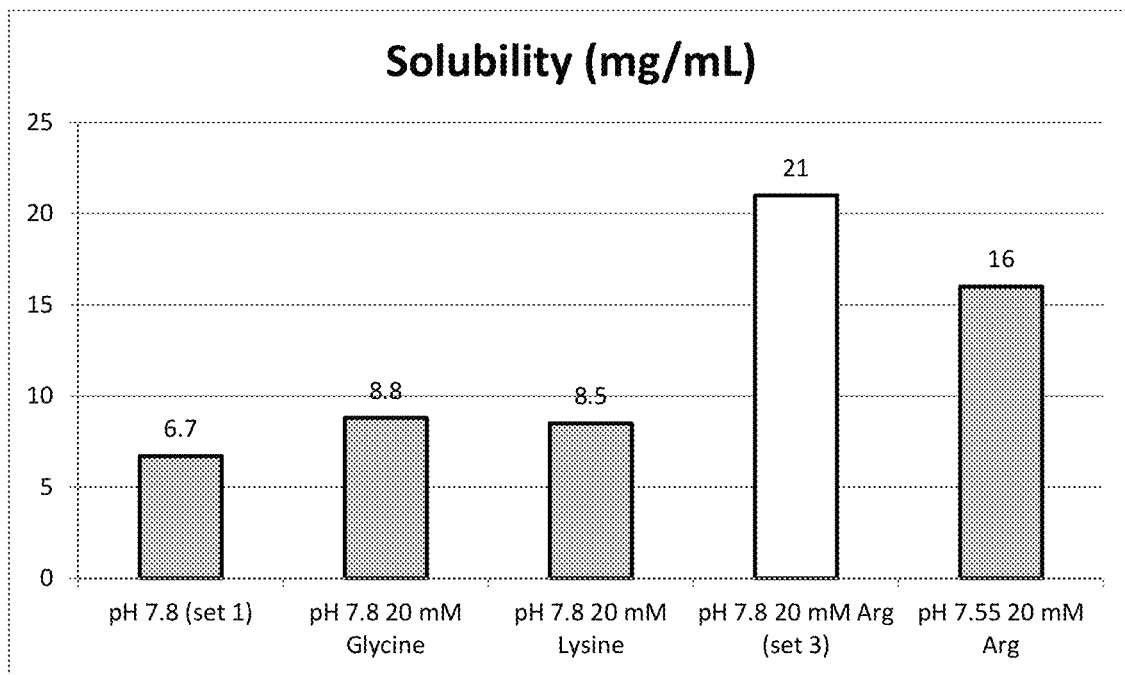

The effect of arginine was also compared to glycine and lysine at pH 7.8 (Table 5.4) and the results shown in FIG. 1E. As shown in the figure, Glycine and Lysine did not have an effect on r-Antidote solubility at 5° C. and more solubilizing effect observed for 20 mM Arg at pH 8.0 vs. pH 7.55 at 5° C.

TABLE 5.4

Samples tested for r-Antidote solubility in glycine, lysine and arginine at pH 7.8

| Sample | Base Composition | Additional Gly/Lys/Arg | pH (±0.02) | Cacl Osm |
|---|---|---|---|---|
| pH 7.80 | 10 mM Na phos, 9.5% sucrose, 0.01% PS80 | n/a | 7.80 | 313 |
| pH 7.8, 20 mM Glycine | 10 mM Na phos, 8% sucrose, 0.01% PS80, 20 mM Gly | 20 mM Gly | 7.80 | 307 |
| pH 7.8, 20 mM Lysine | 10 mM Na phos, 8% sucrose, 0.01% PS80, 20 mM Lys | 20 mM Lys | 7.80 | 327 |
| pH 7.8, 20 mM Arg (set 3) | 10 mM Na phos, 8% sucrose, 0.01% PS80, 20 mM Arg (set 3) | 20 mM Arg | 7.80 | 327 |
| pH 7.55, 20 mM Arg | 10 mM Na phos, 8% sucrose, 0.01% PS80 | 20 mM Arg | 7.55 | 327 |

Figure 1F:
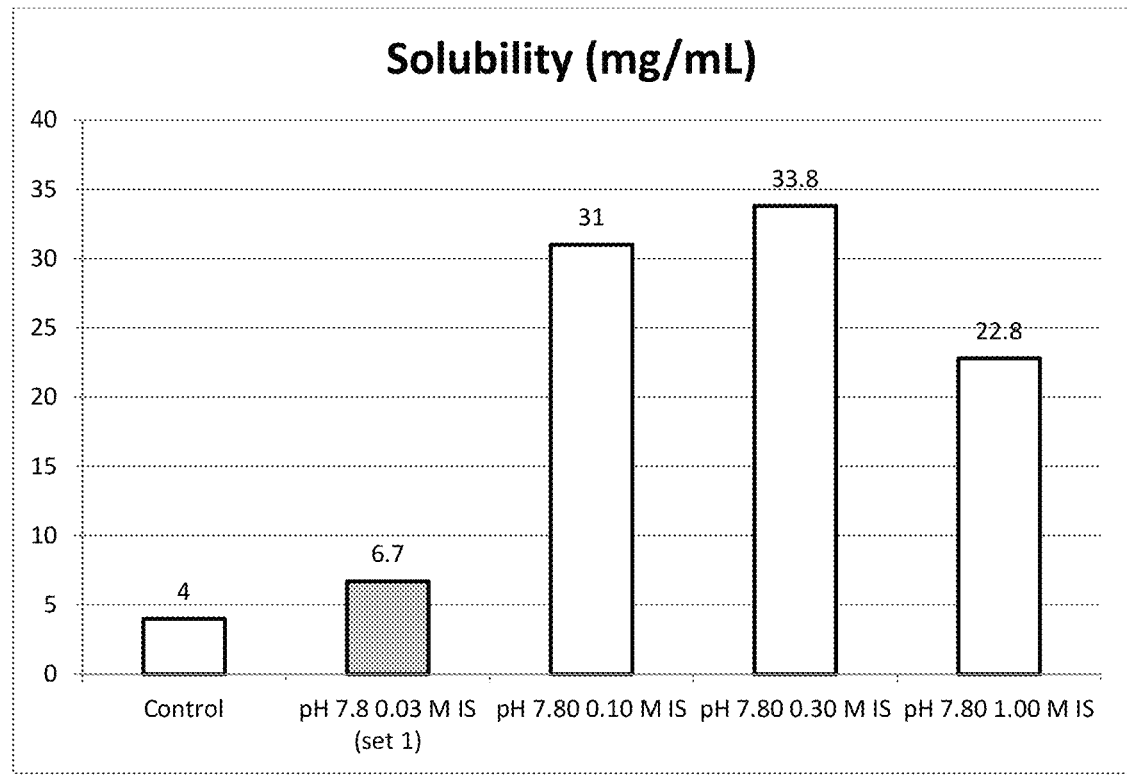

The effect of ionic strength on the solubility of the r-Antidote was also tested (Table 5.5). As shown in FIG. 1F, ionic strength increased r-Antidote solubility at 5° C. in the absence of Arginine or Citrate, and the effect appeared prominent at ionic strength>0.10 M.

TABLE 5.5

Samples tested for r-Antidote solubility at different ionic strength at pH 7.8

| Sample | Base Composition | Additional Gly/Lys/Arg | pH (±0.02) | Cacl Osm |
|---|---|---|---|---|
| pH 7.8, 0.03M IS (set 1) | 10 mM phos, 8% sucrose, 0.01% polysorbate 80, 100 mL | n/a | 7.80 | 277 |
| pH 7.8, 0.03M IS | 10 mM phos, 8% sucrose, 0.01% polysorbate 80, 100 mL | n/a | 7.80 | 277 |
| pH 7.8, 0.10M IS | 10 mM phos, 8% sucrose, 0.01% polysorbate 80, 100 mL | n/a | 7.80 | 417 |
| pH 7.8, 0.30M IS | 10 mM phos, 8% sucrose, 0.01% polysorbate 80, 100 mL | n/a | 7.80 | 817 |
| pH 7.8, 1.00M IS | 10 mM phos, 8% sucrose, 0.01% polysorbate 80, 100 mL | n/a | 7.80 | 2217 |

In summary, this example demonstrates that at room temperature in the absence of a solubilizing agent such as arginine and citrate, the r-Antidote has the highest solubility at pH 8.0. At 5° C., pH 8.0 was the best to the r-Antidote. Further, both citrate and arginine improve the r-Antidote's 5° C. solubility significantly. Glycine and lysine both of which increase the Tm for the r-Antidote, however, has no effect on solubility. Overall, the highest solubility of the r-Antidote at 5° C. was achieved at pH 7.8 with 95 mM Arginine. No precipitation was observed after 10 days.

Example 5. Initial Lyophilization Process

The lyophilization process was developed using a rational approach based on an understanding of the physical nature of the formulation components at different stages of the lyophilization cycle. Thermal characterization methods including DSC and freeze dry microscopy (FDM) were used to measure Tg' (glass transition temperature of the frozen concentrate) and Tc (collapse temperature during primary drying). The cycle shown in Table 6 was selected for lyophilization of the lyophilized formulation. The annealing step allows crystallization of mannitol to ensure that product temperature does not fall below collapse temperature during primary drying. The primary drying temperature was selected to avoid cake collapse with a reasonable duration of primary drying. The 2-step secondary drying condition was developed to produce a lyophilized formulation with a moisture level of <1%.

TABLE 6

Lyophilization Cycle

| Step # | Process Step | Description |
|---|---|---|
| 1 | Freezing | Cooling at 1° C./min to −40° C. |
| 2 | Freezing | Isothermal Hold at −40° C. for at least 180 min |
| 3 | Annealing | Ramp to −20° C. at 1° C./min and hold for at least 180 min |
| 4 | Freezing | Cooling at 1° C./min to −40° C. and hold for at least 180 min |
| 5 | Evacuation | Initiate vacuum to 100 mTorr |
| 6 | Primary Drying | Ramp 0.5° C./min to 10° C. Hold for 40 hours |

TABLE 6-continued

Lyophilization Cycle

| Step # | Process Step | Description |
|---|---|---|
| 7 | Secondary Drying 1 | Ramp to 30° C. at 0.5° C./min, hold for 20 hours at 75 mTorr |

Example 6. Lyophilization without a Crystallizing Component

Experimental/Study Design

Ten different formulations were prepared to test the effects of buffer composition, pH, stabilizer, and drug concentration on the solubility and stability of the r-Antidote (Table 7). The formulations were prepared using Tris or a phosphate buffer at pH 7.8 and 8.2. Solutions were concentrated to 10 mg/mL and 25 mg/mL using centrifugal filtration.

Samples of the concentrated solutions prepared in tris or phosphate buffers were placed on short term stability at 2-8° C. and 25° C. for 2 weeks. At the same time, samples of each solution were used for freeze/thaw studies and examined for precipitation and aggregation. Samples for freeze/thaw studies consisted of 0.5 mL of each formulation in a 2 mL, Type I, glass tubing vial. The 0.5 mL sample was visually inspected prior to freezing and after each freeze/thaw cycle. Each sample was placed at −80° C. for approximately 2 hours, thawed for approximately 15 to 30 minutes at room temperature, visually inspected for approximately 1-2 minutes, and returned to the −80° C. freezer. A 250 L sample of each formulation was removed after the 3rd freezing cycle and submitted to the lab for assays. The remaining solution was subjected to 2 additional freezing cycles and then submitted to the lab for assays.

All remaining solution was lyophilized as 0.25 mL samples using a conservative cycle and the samples were placed on accelerated stability at 25° C. and 40° C.

Two additional formulations were prepared using polysorbate-free solution to test the effects of freeze/thaw and lyophilization on the molecule without the presence of protective agents (Formulations 5 and 6 in Table 7). Samples of the solutions were reserved and used for thermal characterization using modulated DSC and freeze dry microscopy.

TABLE 7

Formulation Numbers, Components, Concentrations, and pH Values

| No. | Components | Concentration | pH |
|---|---|---|---|
| 1A | 10 mM Tris, 4% Sucrose, 95 mM Arginine, PS80 0.01% | 10 mg/mL | 7.8 |
| 1B | 10 mM Tris, 4% Sucrose, 95 mM Arginine, PS80 0.01% | 25 mg/mL | 7.8 |
| 2A | 10 mM Tris, 4% Sucrose, 95 mM Arginine, PS80 0.01% | 10 mg/mL | 8.2 |
| 2B | 10 mM Tris, 4% Sucrose, 95 mM Arginine, PS80 0.01% | 25 mg/mL | 8.2 |
| 3A | 10 mM Phos, 4% Sucrose, 95 mM Arginine, PS80 0.01% | 10 mg/mL | 7.8 |
| 3B | 10 mM Phos, 4% Sucrose, 95 mM Arginine, PS80 0.01% | 25 mg/mL | 7.8 |
| 4A | 10 mM Phos, 4% Sucrose, 95 mM Arginine, PS80 0.01% | 10 mg/mL | 8.2 |
| 4B | 10 mM Phos, 4% Sucrose, 95 mM Arginine, PS80 0.01% | 25 mg/mL | 8.2 |
| 5 | 10 mM Tris, 95 mM Arginine | 25 mg/mL | 7.8 |
| 6 | 10 mM Phos, 95 mM Arginine | 25 mg/mL | 7.8 |

The formulations were prepared using the bulk drug substance supplied at 3 mg/mL, 3.3 mg/mL, and 4.8 mg/mL with and without polysorbate 80 (PS80).

Formulations 5 and 6 were prepared first using 19 mL of the bulk drug solution for each formulation. The volume of bulk was placed in a dialysis cassette having a 10 K membrane and the cassette was placed in 2 L of 10 mM Tris or 10 mM sodium phosphate buffer at pH 7.8. The solutions dialyzed for approximately 2 hours, the dialysis solution was replaced with another fresh 2 L of buffer solution and dialyzed for at least another 2 hours. The solution was removed from each cassette and placed in Amicon Ultra Ultracel 10K centrifugal filter tubes. The solutions were centrifuged for approximately 30 minutes at ¾ speed. The remaining solution was removed from the centrifuge tubes and 95 mM Arginine was added followed by adjusting the pH and volume of the concentrated solution.

The same procedure was used to prepare formulations 1A through 4A and 1B through 4B. Formulations prepared using a bulk solution with 3 mg/mL used 13.5 mL of bulk to prepare the 10 mg/mL solutions and 33.5 mL of bulk to prepare the 25 mg/mL solutions. Formulations that used the 4.8 mg/mL bulk solution used 8.4 mL of the bulk to prepare the 10 mg/mL solution and 20.9 mL of bulk to prepare the 25 mg/mL solution.

The concentrations of sucrose and arginine needed for the final volume of sample solution were added to the bulk solution after concentrating the solution and then the solution was adjusted to the appropriate pH and final volume. PS80 was spiked into the final sample solutions to create a concentration of 0.01% using a 1% solution of PS80.

The solutions were filtered through a 0.22 µm syringe filter and then divided into vials. 2 mL vials were each filled with 250 L of solution and lyophilized using the following conditions:

1. Cool to −40° C. at 1° C./min
2. Hold at −40° C. for 1 hour then initiate vacuum at 100 mTorr
3. Ramp to −35° C. at 0.5° C./min and hold until the Pirani gauge measurement matches the capacitance manometer measurement of 100 mTorr and the product temperature reaches the shelf temperature.
4. Ramp to 20° C. at 0.5° C./min and hold until the Pirani gauge measurement matches the capacitance manometer measurement of 100 mTorr and the product temperature reaches the shelf temperature.

Stoppers were seated and vials were capped after lyophilization. Samples were submitted for initial time point (T0) testing and the remaining vials were placed on stability.

Modulated Differential Scanning Calorimetry (DSC)

The thermal behavior of solution samples was examined using modulated and standard DSC. Samples were examined by placing 12 L of solution into Tzero pans and hermetically sealed. The solutions were cooled to −40° C. at 1° C./min and held isothermally for 5 minutes. The temperature of the samples was ramped to 10° C. at 0.5° C./min with a modulation of 1° C. every 120 seconds. Some samples were examined using an annealing step. Those samples were examined by cooling to −40° C. at 1° C./min, holding isothermally for 5 min, ramping the temperature to −15° C. or −20° C. at 1 to 5° C./min and holding isothermally for at least 60 minutes. The temperature of the samples was returned to −40° C. at 5° C./min, held isothermally for 5 min, and ramped at 0.5° C./min with a modulation of 1° C. every 120 seconds.

Freeze-Dry Microscopy

Samples were examined using freeze-dry microscopy by placing 2 to 4 L of solution between 2 glass coverslips in a Linkam freeze-dry microscope stage. The sample was cooled to −40° C. or lower at 1° C./min and held isothermally for 2 min. Vacuum was initiated at 100 micron and the sample was visually examined using a video camera mounted on a polarized light microscope. The sample was freeze dried at that temperature until dried material was visible and photographed. Afterward, the temperature of the sample was increased in 2° C. increments and held at each temperature to observe the freeze dried sample. The temperature of the sample was increased until complete collapse was observed.

Analytical Methods

A. Concentration by UV-Vis

Concentration of the solutions were measured using a Nano Drop 2000 spectrophotometer (Thermo Scientific). Scans were conducted by placing 2 L of solution on the testing platform and scanning in the range of 280 nm.

B. pH

The pH of solutions was measured using an Orion pH meter model 920A. The meter/probe was calibrated in the range of pH 7 to pH 10 using pre-made buffer solutions purchased from Thermo Scientific.

C. SEC-HPLC

Size Exclusion HPLC analysis was performed using an Agilent 1100 Series HPLC. A mobile phase prepared at 0.1 M Sodium Phosphate, 0.75 M Arginine Hydrochloride at pH 7.4 was used for separation. The analytical column used was an YMC-Pack diol-200, 300×4.6 mm, 5 µm average particle size. The suitability of the HPLC system, including the column, was verified using six replicate injections of reference material and evaluated for retention time, area, and percent area for the main protein peak. Additionally, a gel filtration standard was used to evaluate the separation capability of the column. Samples were diluted to 1 mg/mL protein using the formulation buffer and injected to obtain a column load of 50 µg of protein per injection.

D. RP-HPLC

Reversed Phase HPLC analysis was performed using an Agilent 1100 Series HPLC. The method employs a gradient for separation using mobile phases prepared at 0.1% Trifluoroacetic Acid in HPLC grade water and 0.08% Trifluoroacetic Acid in Acetonitrile. The analytical column used was a Vydac C18 column, 150×4.6 mm, 5 µm average particle size. The suitability of the HPLC system including the column was verified using six replicate injections of reference material and evaluation of retention time, area, and percent area for the main protein peak. Samples were diluted to 1 mg/mL protein using the formulation buffer and injected to obtain a column load of 25 µg of protein/injection.

E. IEX

Ion Exchange HPLC analysis was performed using an Agilent 1100 Series HPLC. The method employs a gradient using mobile phases prepared at 20 mM Sodium Phosphate at pH 6.5 and 20 mM Sodium Phosphate, 1 M Sodium Chloride at pH 6.5. The analytical column used was a Dionex Propac WCX-10, 250×4 mm. The suitability of the HPLC system including the column was verified using six replicate injections of reference material and evaluation of retention time, area, and percent area for the peak labeled as peak #2. Samples were diluted to 1 mg/mL protein using the formulation buffer and injected to obtain a column load of 50 µg of protein per injection.

Results:

A subset of the solution samples were lyophilized using a conservative cycle and placed on stability for 2 months at 25° C. and 40° C. The lyophilization cycle was completed within approximately 20 hours due to the low fill volume. All lyophilized cakes appeared acceptable except for formulation 2A possibly due to a filter tear.

In general, data obtained using SEC and RP appeared to distinguish differences between the formulations. This suggests that the methods are stability indicating and can be used for comparing samples. The data support that the stability of the r-Antidote is affected by pH. The data demonstrate that the stability of formulations prepared at pH 7.8 is better than the stability of formulations prepared at pH 8.2. This is especially true for the samples stored at 40° C.

This study included a comparison of the buffer type on the stability of the r-Antidote. The buffers included tris and phosphate prepared at pH 7.8 and 8.2. The data suggest that buffer type did not affect the stability of the r-Antidote and that differences in stability were mainly a function of pH.

Two formulations in the study (formulations 5 and 6) were prepared without sucrose and polysorbate 80. Sucrose is used as a lyoprotectant and polysorbate 80 is used to prevent aggregation of proteins due to interactions with the walls of the vial and interactions with ice during the freezing step. The formulations prepared without the protectants exhibited increases in percent aggregates as determined by SEC after 1 month of storage at 40° C. The data support the need for the excipients in the formulations to improve the stability of the protein.

The stability study also supports that the lyophilized samples are more stable than the formulations prepared as solutions. Comparison of the solution samples demonstrates that the stability of the solution samples is better when stored at 5° C. than when stored at higher temperatures.

The samples for the stability study were prepared using 0.25 mL per 2 mL vial. Collapse was only observed when there were insufficient solids present to support a cake in sample 2A. All other samples appeared acceptable, however it was not feasible to determine the extent of cake shrinkage when using such low fill volumes. Thermal characterization studies were conducted concurrently with the stability studies to determine the feasibility of lyophilizing the formulations at full scale.

Formulations 5 and 6 were examined using modulated DSC. Both formulations contain approximately 25 mg/mL the r-Antidote and 95 mM arginine HCl, but formulation 5 was prepared with 10 mM Tris and formulation 6 was prepared with 10 mM phosphate. No thermal events were observed during the warming ramp when observed using total heat flow, non-reversing heat flow, or reversing heat flow. A total heat flow thermogram will show both kinetically related events and non-kinetically related events. Non-reversing heat flow thermograms will show kinetically related events such as crystallization and reversing heat flow thermograms will show non-kinetically related events such as glass transitions. The lack of observable events may suggest that the concentrations of the components are too low to produce a signal with sufficient intensity.

Freeze dry microscopy experiments were conducted to determine if the collapse temperature would match the results observed for the Tg' determined using MDSC. The thermal behavior of the all of the samples was expected to be similar because all had the same excipients at similar concentrations.

Formulations 5 and 6 were prepared with a r-Antidote concentration of approximately 25 mg/mL and both contained 95 mM arginine at pH 7.8. The only difference between the formulations was the buffer. Formulation 5 contained 10 mM tris and formulation 6 contained 10 mM phosphate. Formulation 5 exhibited collapse at −40° C. and formulation 6 exhibited collapse at −39° C. The data support that the temperature of the product need be maintained below the determined collapse temperature to obtain acceptable lyophilized samples. Maintaining such low product temperatures is not feasible in laboratory or full scale lyophilizers.

Although the stability data for the lyophilized formulations appeared acceptable, the thermal characterization data demonstrated that the formulation was not amenable to scale-up due to the low collapse temperature. Thermal characterization obtained using MDSC and freeze dry microscopy suggest that the formulations remain amorphous after freezing and drying and that the combination of components leads to a low collapse temperature. The only way to create a formulation that is amenable to scale up is to add a crystallizing component to serve as a scaffold that can hold the amorphous material in place during and after freeze drying. The most common crystallizing component added to pharmaceutical formulations is mannitol. All further formulation and process development work investigated the addition of mannitol at different concentrations. The development of a formulation containing mannitol and the stability studies for the formulations are described in a separate development report.

Conclusion

The effects of buffer type, pH, stabilizer, and protein concentration on the stability of the r-Antidote were examined as solution and lyophilized formulations. Solution samples were stored at 5° C. and 25° C. for up to 2 weeks and lyophilized samples were stored at 25° C. and 40° C. for up to 2 months. Formulations lyophilized as 0.25 mL in 2 mL vials exhibited acceptable stability after 2 months. However, thermal characterization experiments demonstrated that all formulations had collapse temperatures of −37° C. or lower and were not amenable to scale-up. The data suggest that a crystallizing component is needed in the formulation to prevent collapse and to allow for lyophilizing at higher temperatures.

Example 7. Effect of Buffer Type and Mannitol on the Thermal Behavior and Stability of the Formulation.

Data from Example 6 suggested that a crystallizing component was needed in the r-Antidote formulation to prevent collapse during freeze drying. This example examined the effects of mannitol and arginine concentrations on the thermal behavior and lyophilized cake appearance of the formulations. Formulations containing 2% to 4% mannitol were investigated along with reducing the concentration of arginine. Arginine prevented the crystallization of mannitol unless the concentration was 47.5 mM or less. Studies found that a formulation containing 10 mM tris, 10 mg/mL r-Antidote, 45 mM arginine, 2% sucrose, 5% mannitol, and 0.01% polysorbate 80 resulted in lyophilized cakes with acceptable appearance, and physical and chemical stability. Lyophilization studies provided data to support using a primary drying shelf temperature of −25° C. after annealing at −25° C. for 3 hours. A two-step secondary drying process results in cakes with residual moisture values less than 1%.

Experimental/Study Design

Studies were designed to concurrently examine the thermal behavior of the formulations and compare the chemical stability of formulations that were lyophilized using a conservative cycle. The initial formulations were prepared with 95 mM arginine, 2% sucrose, 2% mannitol, and either 10 mM tris or 10 mM phosphate buffers at pH 7.8. The formulations also contained the active ingredient at either 10 or 25 mg/mL (Table 8.1).

TABLE 8.1

Initial Formulations Prepared with Mannitol at pH 7.8.

| Formulation ID | Arginine (mM) | Tris (mM) | Phosphate (mM) | Sucrose (%) | Mannitol (%) | r-Antidote (mg/mL) |
|---|---|---|---|---|---|---|
| TM1 | 95 | 10 | | 2 | 2 | 10 |
| TM2 | 95 | 10 | | 2 | 2 | 25 |
| PM1 | 95 | | 10 | 2 | 2 | 10 |
| PM2 | 95 | | 10 | 2 | 2 | 25 |

Aliquots of the thawed drug solution were placed in dialysis cassettes with 3K molecular weight cut off (MWCO) membranes. The cassettes were placed in the buffer solutions containing either tris or phosphate with arginine, sucrose, and mannitol. Each cassette containing the drug solution was placed in 2L of buffer solution and dialyzed for 4 hours. The buffer solution was refreshed after 2 hours and the solutions were dialyzed for another 4 hours or overnight at 2-8° C. The solutions were removed from the dialysis cassettes using BD syringes with 18G needles and placed in centrifugal filtration tubes with 3K MWCO membranes. The tubes were centrifuged at approximately 3000 RPM for 20 to 30 minutes and the concentrations of the solutions were checked using a NanoDrop 2000 spectrophotometer. Solutions were concentrated to greater than 10 mg/mL or 25 mg/mL and diluted to the appropriate concentrations using the appropriate buffer solution and the polysorbate concentration was adjusted to 0.01% using a 1% solution of polysorbate 80. The solutions were filtered through 0.22 μm syringe filters and filled into 3 mL glass, tubing vials at 0.25 mL and 0.8 mL per vial. The solutions were freeze dried using a conservative cycle (Table 8.2) and placed on stability at 25° C. and 40° C. for up to 2 months.

TABLE 8.2

Conservative Lyophilization Cycle Used for Mannitol Containing Formulations.

| Step | Details |
|---|---|
| Freezing | Ramp 1° C./min to −40° C. |
| Isothermal | Hold 120 min |
| Annealing | Ramp 1° C./min to −25° C., Hold 180 min |
| Primary Drying | −30° C., Hold until Pirani = CM |
| Secondary Drying | Ramp 0.5° C./min to 40° C., Hold until Pirani = CM |

Samples of each solution prior to freeze drying were reserved for thermal analysis using DSC and FDM.

Additional thermal analyses and lyophilization cycle development studies were completed using the buffer solutions prepared without the protein. The experiments were conducted to determine the minimum concentration of arginine needed in the formulation to solubilize the protein while not interfering with the crystallization of mannitol. Solubility studies were conducted by the client to determine the minimum concentration of arginine needed to solubilize the protein.[1] Experiments were conducted by Baxter to test the effect of arginine and mannitol concentration on thermal behavior, lyophilization cycle conditions, and cake appearance. The buffer solutions contained 10 mM of tris with 2% sucrose at pH 7.8. The arginine concentrations varied from 95 mM to 9.5 mM and the mannitol concentrations were varied between 2% and 5%.

Good formulation candidates were identified based on thermal behavior, cake appearance, and short term accelerated stability data. The proposed formulation for further development contains 10-25 mg/mL r-Antidote, 10 mM tris at pH 7.8, 45 mM arginine, 2% sucrose, 5% mannitol, and 0.01% polysorbate 80. Early studies used 0.2 mL to 1 mL per 3 mL vial. The initial stability study using a low arginine formulation was conducted using a drug concentration of 25 mg/mL and lyophilized using a conservative cycle. The samples were placed on stability at 25° C. and 40° C. for up to 3 months.

Cycles conducted to confirm the process used drug solution filled into 10 mL vials at 5 mL per vial. The same vial and fill volume were used for studying the effect of moisture content during studies of secondary drying. The formulations for these studies were prepared using drug solution that was exchanged into the appropriate buffer using a laboratory-scale tangential flow filtration (TFF) unit. The TFF unit was equipped with a holding vessel for the solution that was connected to the tangential flow filter with tubing. The vessel was filled with drug solution, exchanged into the appropriate buffer, and concentrated to 10 to 25 mg/mL by filtering through a 10 KDa MWCO membrane. A sufficient quantity of 1% polysorbate 80 (PS80) was added to create a 0.01% PS80 concentration. The final solution was filtered through a 0.22 μm syringe filter or vacuum filtration system.

The lyophilization cycles examined process parameters such as the cooling ramp rate and the ramp rate between primary and secondary drying as well as the shelf temperature during annealing and primary drying. A residual moisture study was conducted by removing samples at the beginning of secondary drying and after 4, 8, and 10 hours at 40° C. A second study was conducted by removing samples after 8 hours at 40° C. and after 1 and 2 hours at 50° C. The samples were tested for residual moisture using Karl Fischer analysis and drying was considered complete when the values for residual moisture reached a plateau. The effect of the residual moisture on the stability of the formulation was tested by removing samples at times during secondary drying that corresponded to specific residual moisture values. The samples were placed on stability at 40° C. for up to 2 months and at 50° C. for 1 week.

A lyophilization cycle design space was created for proposed drug product formulation containing 10 mg/mL r-Antidote, 10 mM tris, 45 mM arginine, 2% sucrose, 5% mannitol, and 0.01% polysorbate 80 at pH 7.8. The formulation was filled into 10 mL glass, tubing vials using 5 mL solution per vial. Development of the design space requires knowledge of the equipment capability combined with the collapse temperature of the formulation and the heat transfer coefficient for the vial. The heat transfer coefficient for the vial was determined using the exact glass, tubing vial used for the product, filling the vials with water, and subliming the ice using the shelf temperature intended for drying the product. Product temperature and mass flow data were collected while varying the chamber pressure from approximately 25 mTorr to approximately 400 mTorr. Mass flow data were collected at each pressure using tunable diode laser absorption spectroscopy (TDLAS) and the change in mass flow rate with pressure is used to calculate the heat transfer coefficient for the vial.

Results:

1. Differential Scanning Calorimetry (DSC)

Individual solutions of each buffer component were prepared and tested using DSC to determine the influence of each component on the thermal behavior of the buffer formulation. Typically, the thermal behavior of the formulation is dictated by the component present at the highest concentration. Changes in the thermal behavior can occur with the addition of other excipients or the drug. For example, the addition of salts can decrease the Tg' of amorphous materials in the formulation. The proposed drug formulation contains mannitol. Mannitol is added as an excipient to lyophilized formulations to serve as a crystallizing bulking agent. Mannitol is amorphous when initially frozen in a solution. An annealing step is typically included during freezing to encourage crystallization of mannitol so that it can provide structure for the cake. Other excipients and/or the active ingredient in a formulation can prevent or delay the crystallization of mannitol. The studies discussed in this section investigated the effects of tris, phosphate, and arginine on the crystallization of mannitol and the thermal behavior of the solution.

Figure 2:
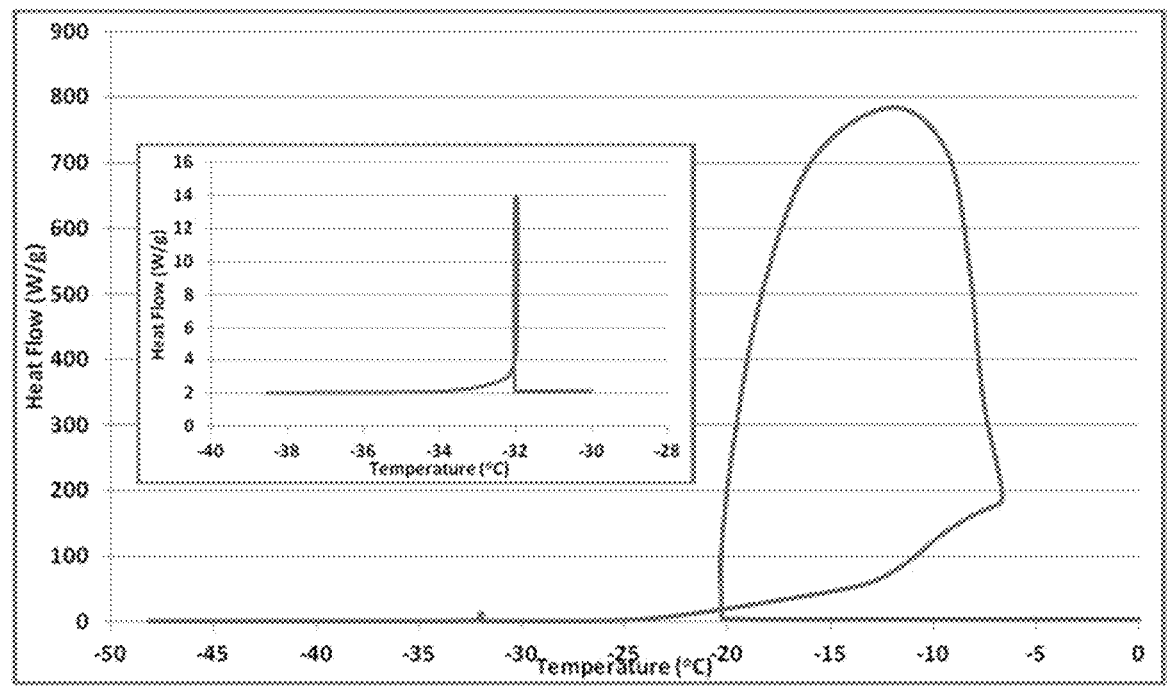
FIG. 2 is a DSC heat flow thermogram for 10 mm tris solution showing cooling at 1° C./min and the crystallization exotherm for tris at −32° C.

A 10 mM tris solution prepared at pH 7.8 was cooled at 1° C./min to −50° C. (FIG. 2) using DSC. The thermogram shows the crystallization exotherm for ice starting at approximately −20° C. followed by the crystallization exotherm for tris at −32° C.

Figure 3:
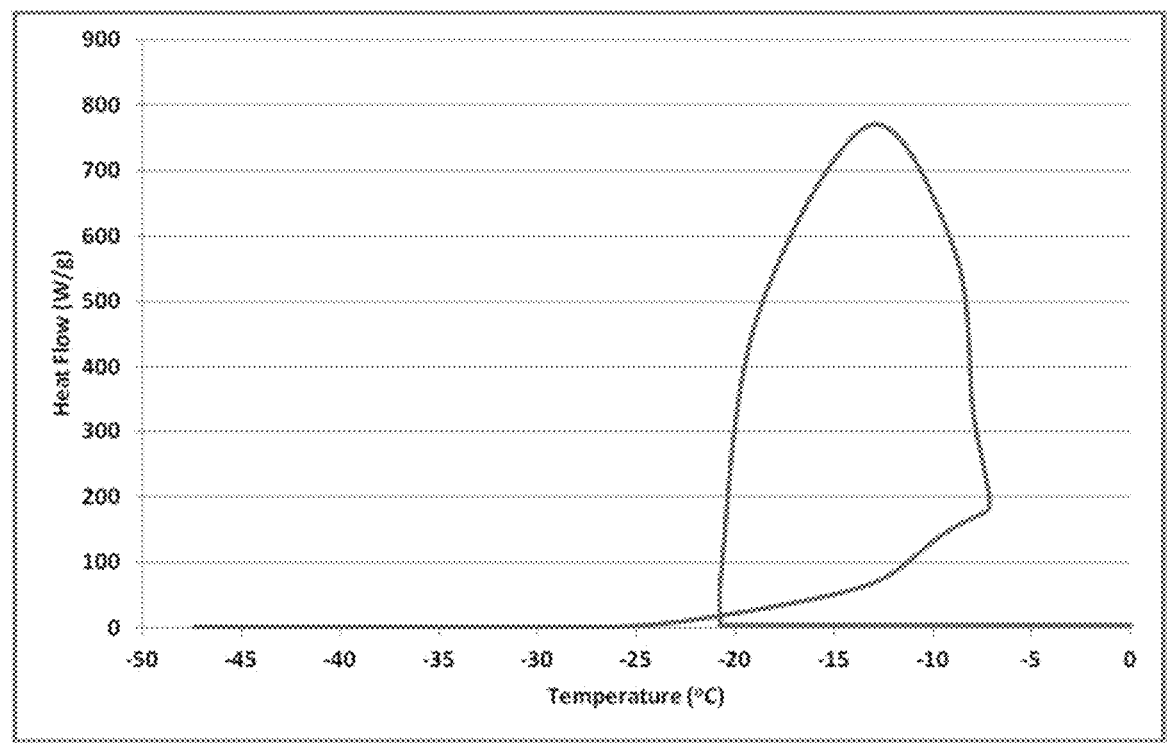
FIG. 3 is a DSC thermogram during cooling of 10 mm tris with 95 mm arginine. No crystallization exotherm for tris.

The crystallization exotherm is no longer present when 95 mM arginine is included in the formulation (FIG. 3). No thermal events besides the melting endotherm for ice were observed within the temperature range for this study.

A Tg' with a midpoint of approximately −42° C. is observed when the 10 mM Tris, 95 mM arginine formulation contains 4% sucrose. The midpoint of the Tg' for sucrose alone is typically around −33° C. The study demonstrates that the tris/arginine mixture decreases the Tg' for sucrose. A solution with a Tg' below −40° C. is not a good candidate for lyophilization. It is difficult to maintain such a low product temperature during primary drying. The addition of a crystallizing component, such as mannitol, can provide structure and improve the chances of lyophilization as long as mannitol crystallizes before the start of primary drying.

Figure 4:
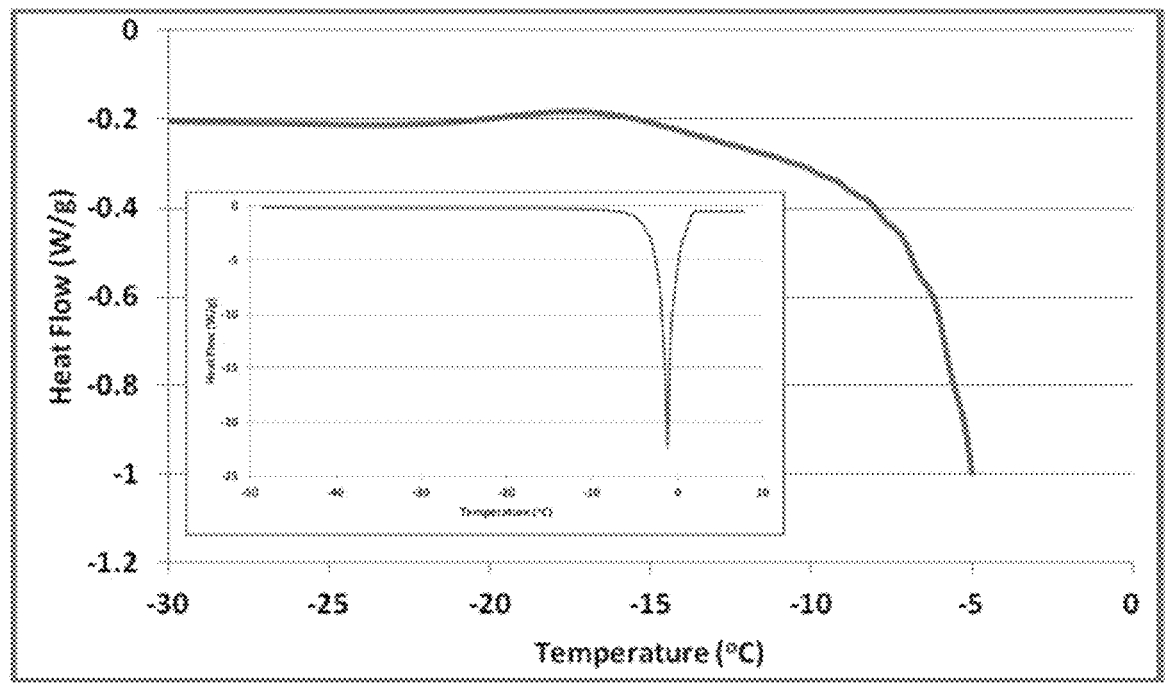
FIG. 4 is a DSC thermogram for a solution containing 10 mm tris, 2% sucrose, and 2% mannitol showing crystallization of mannitol at approximately −18° C.
Figure 5:
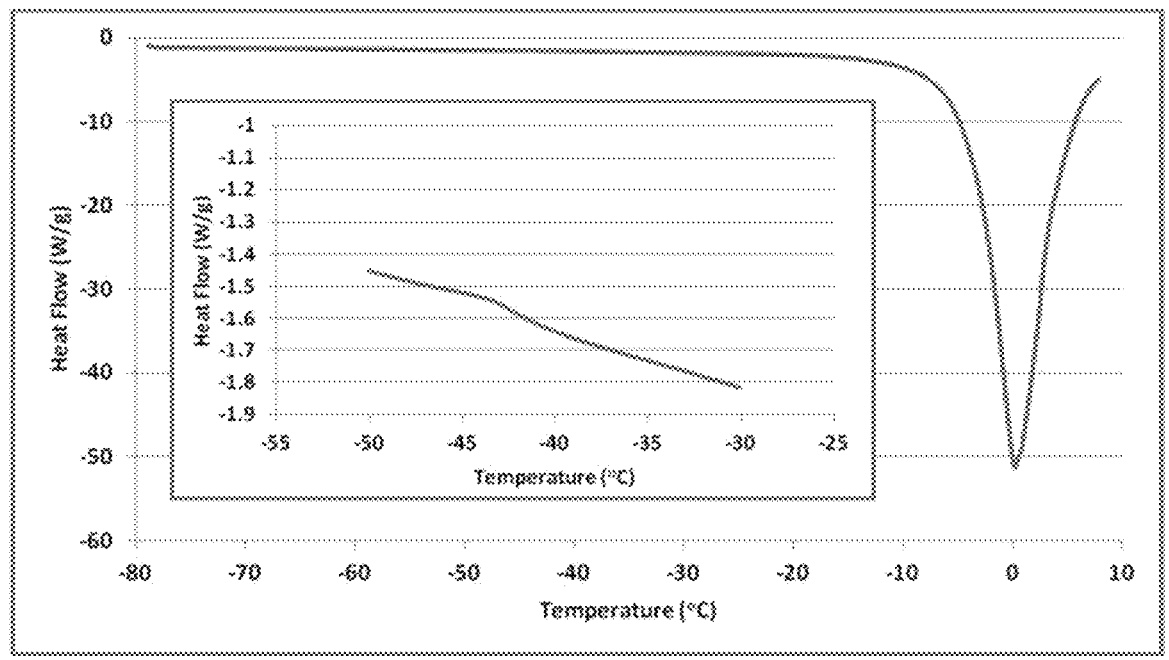
FIG. 5 is a DSC thermogram for a solution of 10 mm tris, 95 mm arginine, 2% sucrose, and 2% mannitol showing the tg' for sucrose at −42° C. solution was annealed for 5 hours at −20° C.
Figure 6:
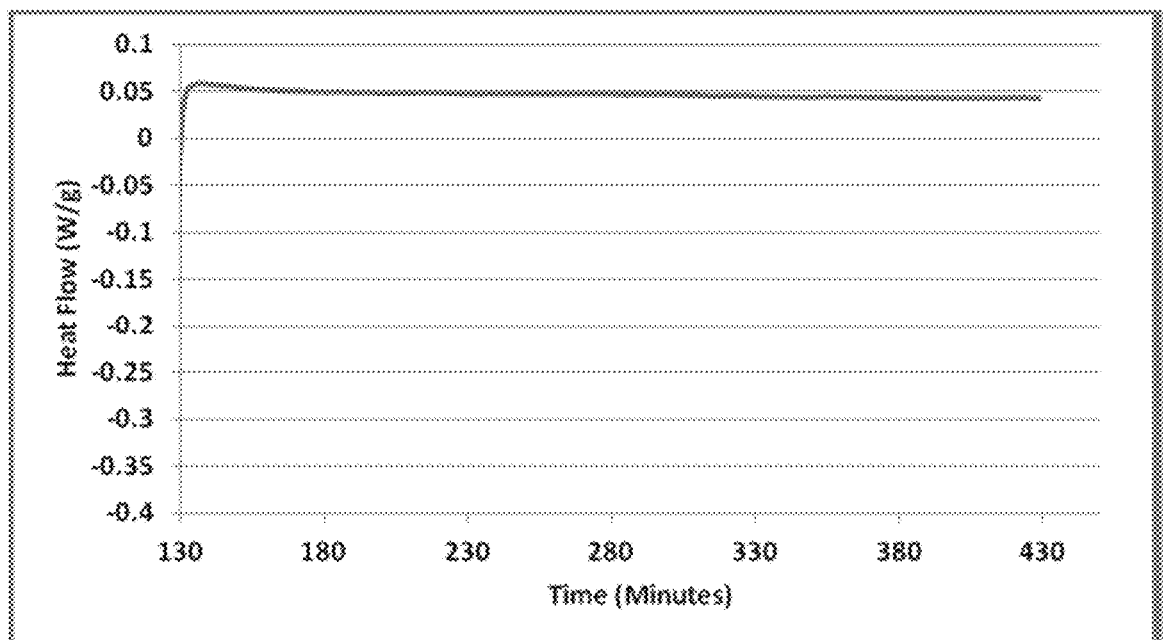
FIG. 6 is a DSC thermogram for a solution of 10 mm tris, 95 mm arginine, 2% sucrose, and 2% mannitol showing the annealing step at −20° C. for 5 hours with no evidence of a crystallization exotherm.

Mannitol was added to the formulation at 2% W/V and the sucrose concentration was reduced to 2% so that the total sugar content in the formulation was maintained at 4%. A solution prepared with 10 mM tris, 2% sucrose and 2% mannitol demonstrates that mannitol will begin to crystallize at approximately −20° C. (FIG. 4). The crystallization of mannitol is prevented when 95 mM arginine is added to the solution (FIG. 5). Mannitol did not crystallize even when the frozen solution was annealed at −20° C. for up to 5 hours (FIG. 6).

Figure 7:
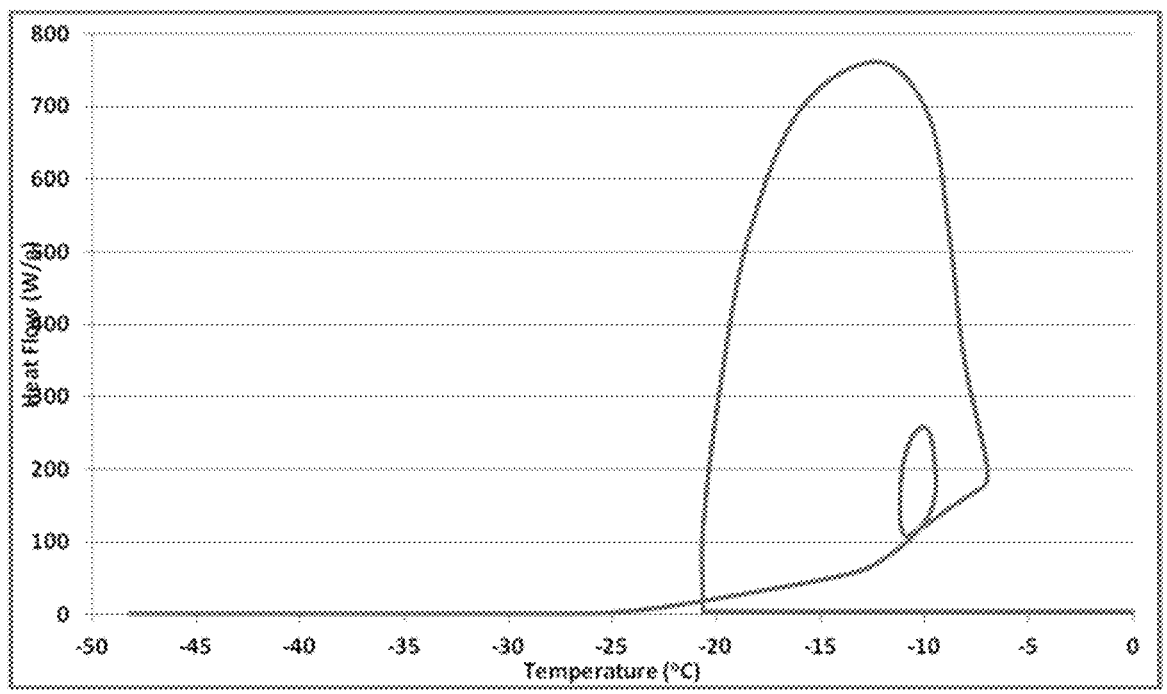
FIG. 7 is a DSC thermogram for 10 mm sodium phosphate solution showing a crystallization exotherm for sodium phosphate at approximately −10° C.

The same set of thermal analyses was conducted for solutions prepared with 10 mM sodium phosphate to test the effect of the buffer on the thermal behavior of the formulation. Sodium phosphate crystallized during the cooling step (FIG. 7) when prepared as a 10 mM solution at pH 7.8.

A mixture of 10 mM sodium phosphate with 95 mM arginine and 4% sucrose exhibits a Tg' with a midpoint at approximately −38° C.

Figure 8:
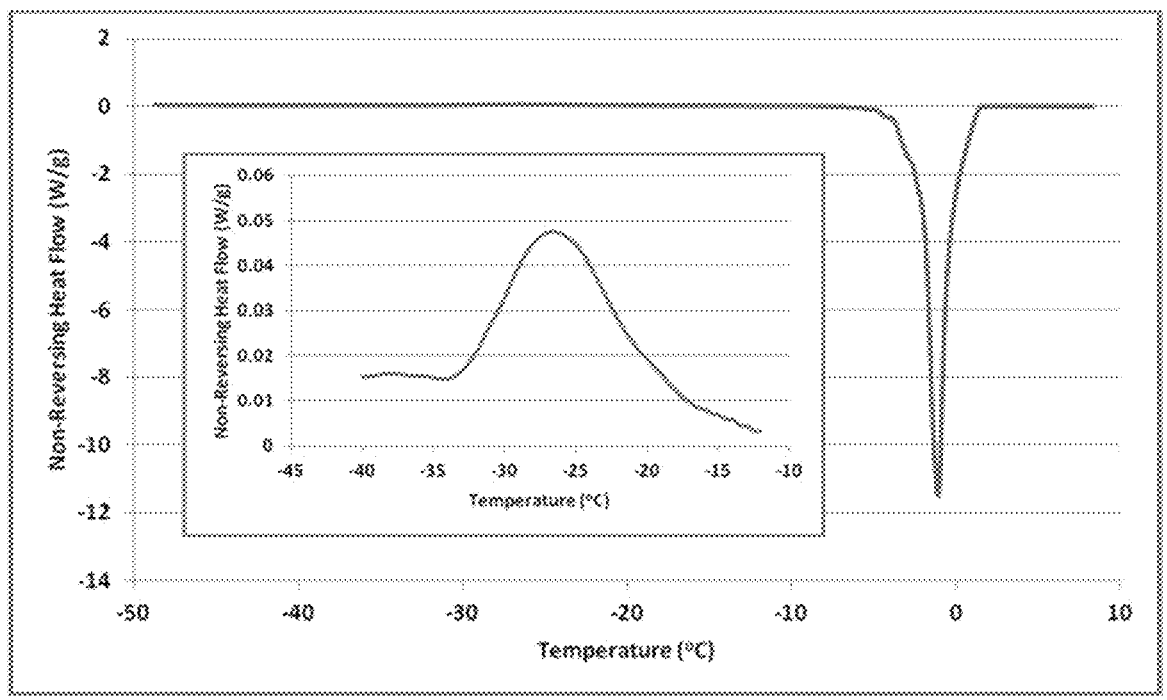
FIG. 8 is a DSC non-reversing heat flow thermogram for 10 mm sodium phosphate with 2% sucrose and 2% mannitol showing a crystallization exotherm with an onset at approximately −33° C.
Figure 9:
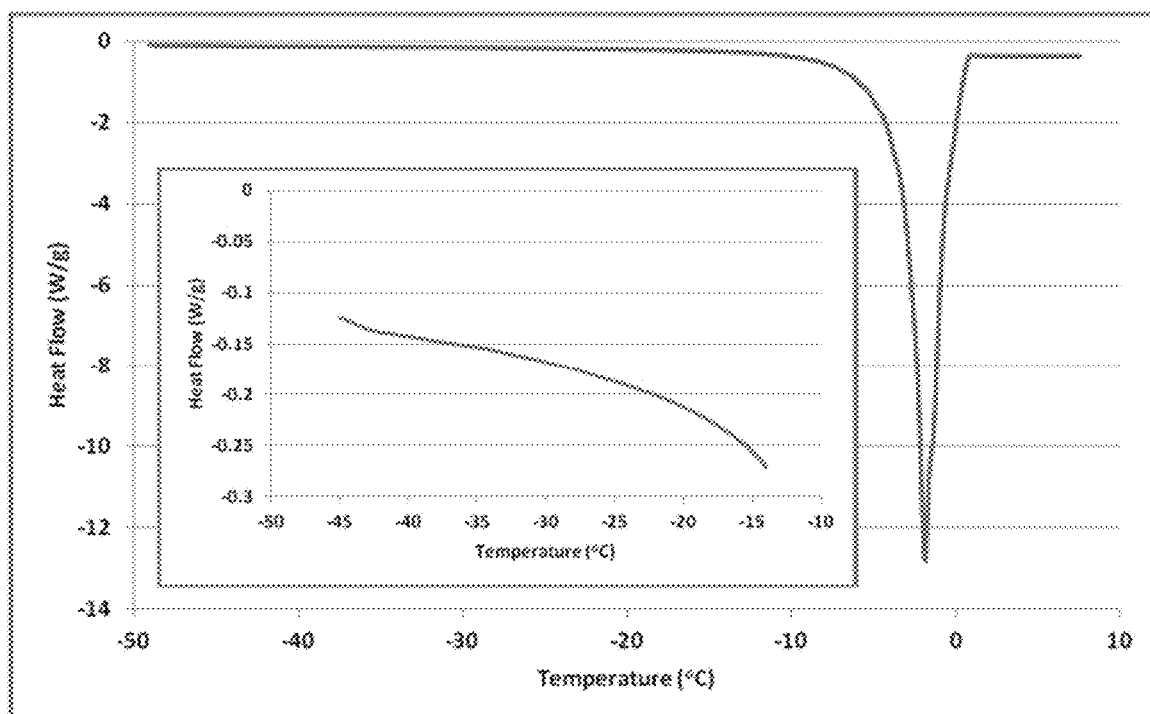
FIG. 9 is a DSC heat flow thermogram for 10 mm sodium phosphate, 95 mm arginine, 2% sucrose, and 2% mannitol exhibiting no thermal events besides the ice melting endotherm.

Similar to the tris solutions, phosphate solutions containing sucrose and mannitol exhibit a crystallization exotherm for mannitol (FIG. 8). The crystallization exotherm is not observed when 95 mM arginine is added to the mixture (FIG. 9). Similar to the formulation prepared with tris, no crystallization exotherm was observed for mannitol even when the phosphate formulation was annealed at −20° C. for 5 hours.

The studies demonstrate that the addition of 95 mM arginine to formulations containing either tris or phosphate will drastically decrease the Tg' for sucrose and will prevent the crystallization of mannitol. The data demonstrated that a change to the formulation was necessary in order to encourage crystallization of mannitol for a successful lyophilized cake. At the time of this study, data suggested that either 95 mM arginine or 10 mM to 20 mM citrate were needed to maintain the solubility of the protein. Therefore, studies were conducted using solutions containing 10 mM or 20 mM citrate in 10 mM tris with 2% sucrose and 5% mannitol as an alternative to arginine in the formulation. The mannitol concentration was increased and the sucrose concentration was decreased to increase the likelihood of mannitol crystallization. Studies using 2% sucrose with 5% mannitol along with arginine are described later in this report.

Figure 10:
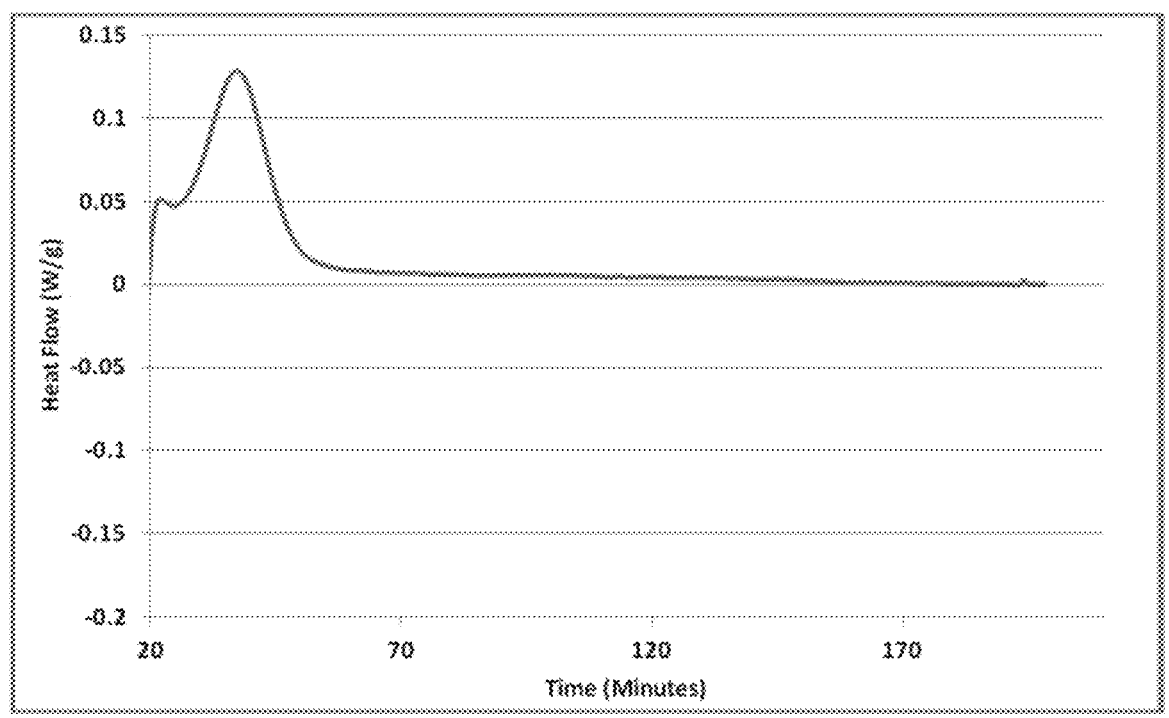
FIG. 10 is a DSC heat flow thermogram for 10 mm tris, 10 mm citrate, 2% sucrose, and 5% mannitol showing a crystallization exotherm with an onset of approximately 24 minutes at −25° C.
Figure 11:
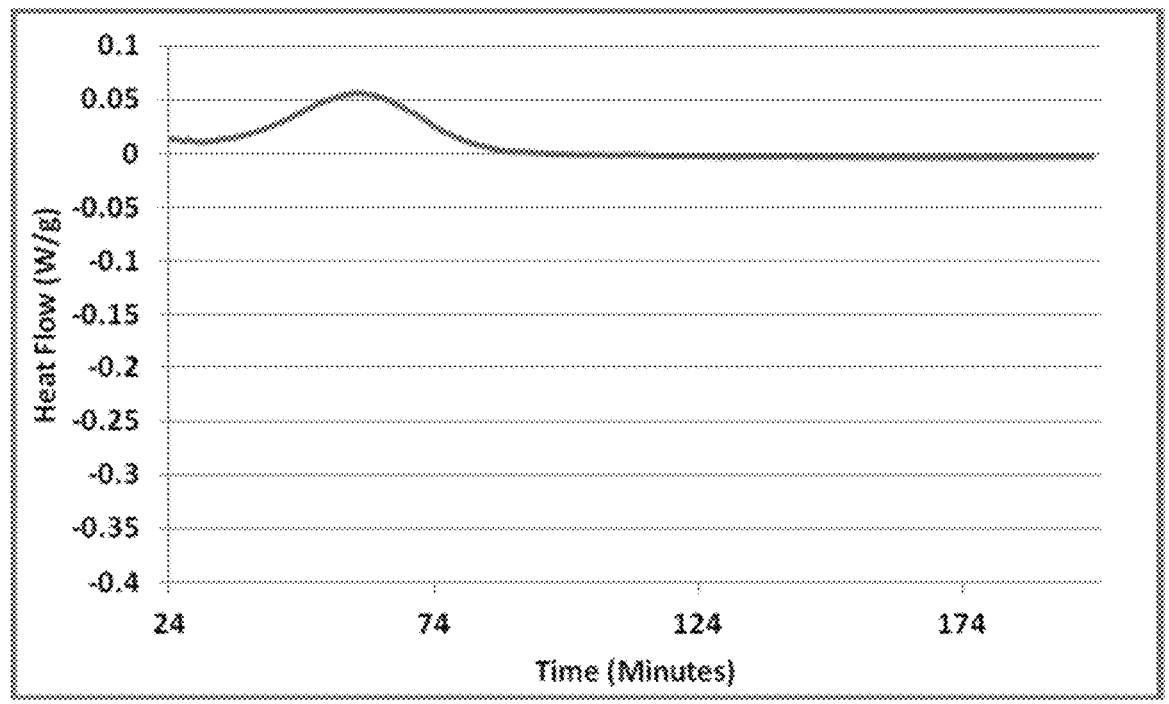
FIG. 11 is a DSC heat flow thermogram for 10 mm tris, 20 mm citrate, 2% sucrose, and 5% mannitol showing a crystallization exotherm with an onset of approximately 30 minutes at −25° C.

The solutions containing citrate were annealed at −25° C. A crystallization exotherm was observed with an onset of 24 minutes in 10 mM citrate at −25° C. (FIG. 10) and an onset of 30 minutes in 20 mM citrate at −25° C. (FIG. 11).

2. Freeze Dry Microscopy (FDM)

The formulations prepared with 10 mM phosphate or 10 mM tris with 10 mg/mL r-Antidote, 95 mM arginine, 2% sucrose, and 2% mannitol at pH 7.8 were examined using FDM. Experiments conducted with the tris formulation showed an onset of collapse for the formulation at approximately −34° C. when annealed at −25° C. for up to 3 hours.

The formulation containing 10 mM phosphate had a higher collapse temperature. A consistent dry layer was observed at −32° C. and the onset of collapse was observed at −30° C.

The FDM data suggest that both formulations can be lyophilized using conditions that are amenable to routine production. This does not correlate with data obtained using DSC. Experiments conducted using FDM utilize thin layers of solution between two glass coverslips in direct contact with a temperature controlled stage. These conditions suggest an ease of drying and, therefore, failed to correlate with the DSC data, which were relied upon for subsequent testing given its relevance.

3. Lyophilization and Stability

The phosphate and tris formulations prepared with 10 mg/mL and 25 mg/mL r-Antidote, with 95 mM arginine, 2% sucrose, and 2% mannitol at pH 7.8 were examined on stability as solutions and lyophilized samples. Each solution was filled into 3 mL vials at 0.20 mL per vial. A portion of the samples was stored at 5° C. and 25° C. for up to 2 weeks and the other portion of the samples was lyophilized using a conservative cycle and placed on stability at 25° C. for up to 3 months and at 40° C. for up to 2 months.

The samples were annealed at −25° C. for 1 hour before lyophilizing at −30° C. Secondary drying was conducted also using conservative conditions with a 20° C. shelf temperature. A conservative, non-conventional cycle was used because little was known about the temperature sensitivity of the protein. The lyophilization cycle was completed within approximately 21 hours. The vials were sealed with stoppers before removing from the lyophilizer, capped, and placed on stability.

The lyophilized cakes appeared acceptable with no evidence of collapse and reconstituted rapidly with purified water. A second study using the same formulations without the drug was conducted concurrently to ensure that the crystallization of mannitol, if it occurred, did not result in breakage of vials. The placebo formulations were filled into 20 mL vials with 10 mL of solution each. One full tray of vials was cooled to −40° C. at 1° C./min, held isothermally for 120 minutes, and then ramped to −25° C. at 1° C./min for 3 hours of annealing. A second set of vials was cooled to −25° C., held isothermally for 3 hours, cooled to −35° C. and then transferred to the dryer containing the full tray of vials. All vials were lyophilized at −30° C. and dried at 25° C. for secondary drying. Collapse was observed in vials containing both formulations.

This suggests that the mannitol did not crystallize and supports the conclusion made during thermal analysis using DSC that arginine was preventing the crystallization of mannitol. Therefore, the DSC and lyophilization data, given their relevance to the formulation development, rather than the FDM results, were relied upon for future experiments.

Studies described in the next example focused on the reduction of arginine and its effect on the solubility of the protein and crystallization of mannitol. The phosphate and tris formulations prepared with 95 mM arginine described above remained on stability to provide initial data.

Figure 12:
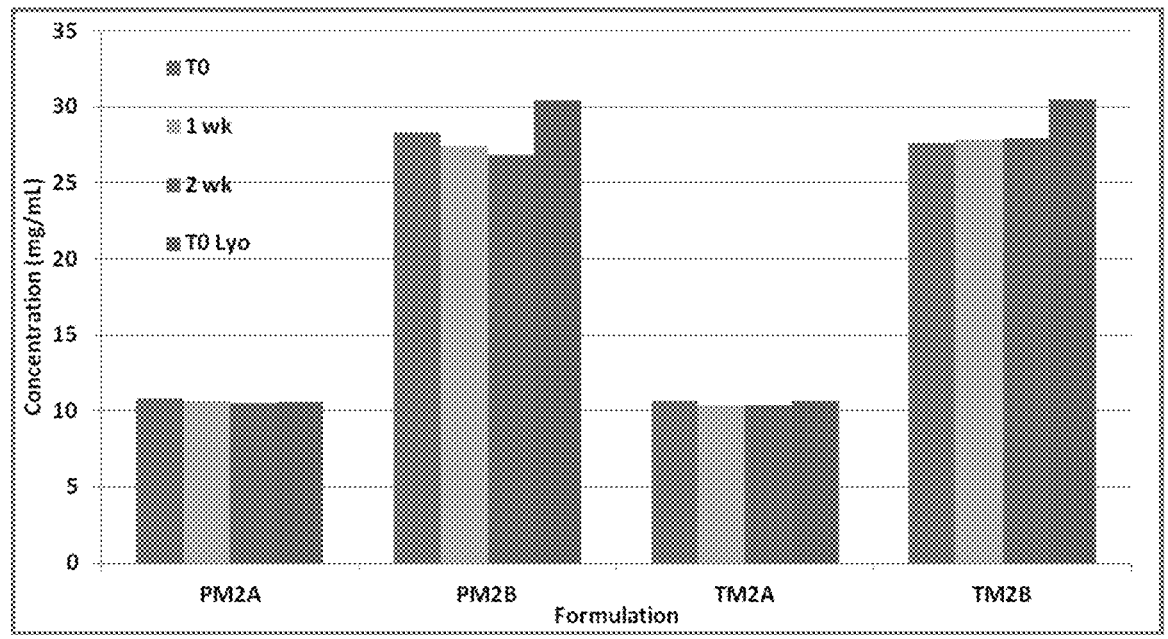
FIG. 12 is a UV concentration data for tris and phosphate solution formulations stored at 5° C. for up to 2 weeks compared with lyophilized formulations at T0.
Figure 13:
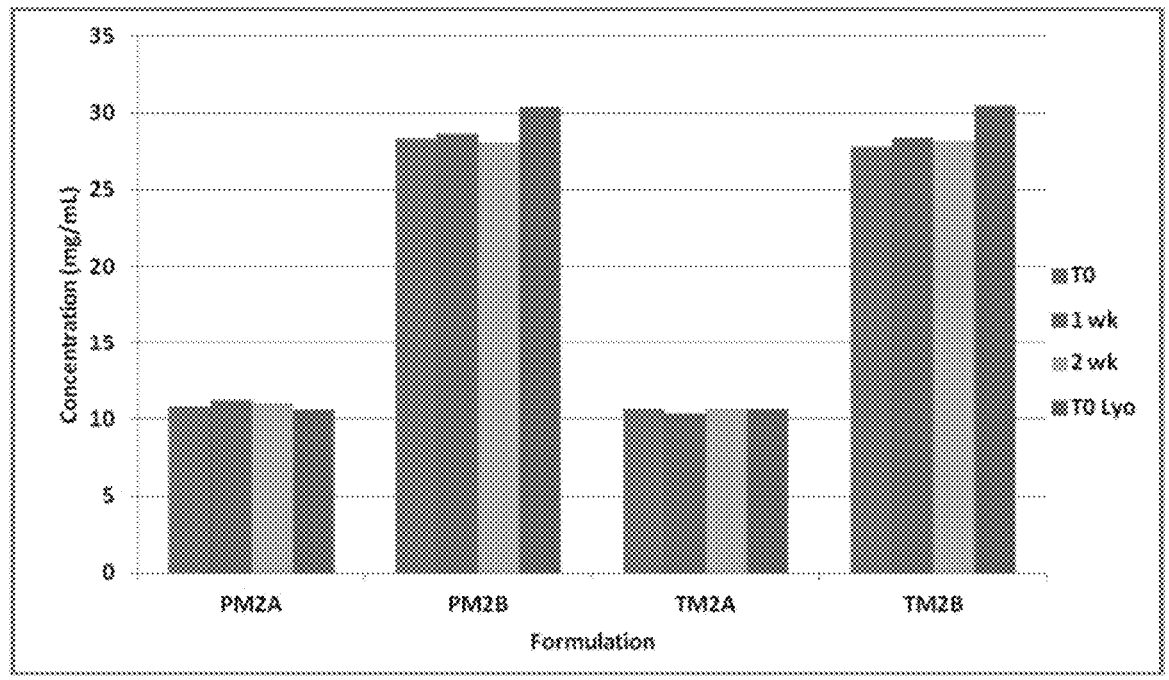
FIG. 13 is a UV concentration data for tris and phosphate solution formulations stored at 25° C. for up to 2 weeks compared with lyophilized formulations at T0.

No loss in concentration was observed in the solution samples when stored at 5° C. and 25° C. for up to 2 weeks and there was no difference in concentration between the liquid and lyophilized samples at T0 (FIGS. 12 and 13).

Figure 14:
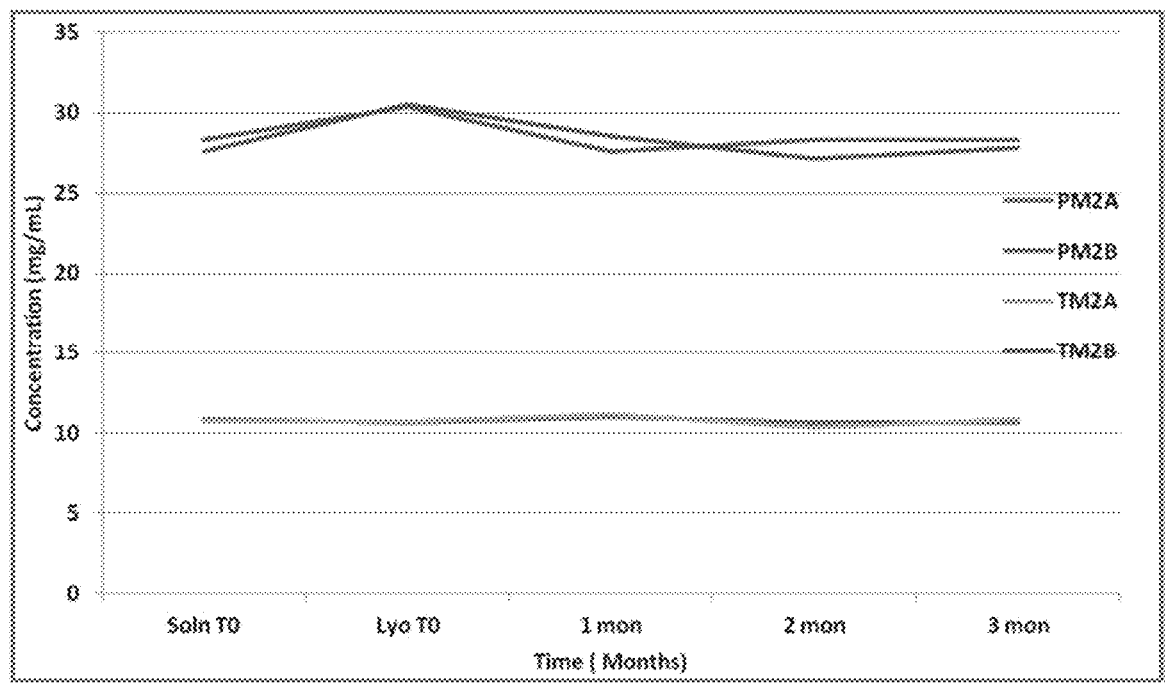
FIG. 14 is a UV concentration data for tris and phosphate lyophilized formulations stored at 25° C. compared with solution formulations at T0.

Similarly, no losses in concentration were observed in any of the lyophilized formulations stored at 25° C. for up to 3 months (FIG. 14) or at 40° C. for up to 2 months.

SEC data show that there were no losses in main peak when the solution formulations were stored at 5° C. for up to 2 weeks. The percent main peak decreased by greater than 1% in 10 mg/mL samples and by greater than 3% in 25 mg/mL samples when stored at 25° C. for up to 2 weeks.

Therefore, although the chemical stability of the formulations appears acceptable, changes to the formulation were necessary due to the poor physical stability during lyophilization. Poor physical stability was demonstrated by the collapsed cakes observed for the placebo formulation. Data from DSC experiments suggest that decreasing the arginine concentration and increasing the mannitol concentration should encourage crystallization of mannitol and improve the physical stability of the lyophilized cake.

Example 8. Effects of Arginine and Mannitol Concentrations on the Thermal Behavior and Appearance of the Lyophilized Samples This example was conducted to investigate the effects of arginine concentration and mannitol concentration on the thermal behavior and cake appearance using placebo formulations. The studies focused on placebo formulations prepared with a tris buffer. Tris buffer was chosen because it is the buffer used to prepare the bulk drug solution and because there was no difference in the chemical stability of samples prepared with tris and sodium phosphate.

The following studies examined using an arginine concentration range of 9.5 mM to 95 mM and a mannitol concentration range of 2% to 5%.

1. Thermal Analysis

The goal of the thermal analysis experiments was to determine the concentrations of arginine and mannitol that encouraged crystallization of mannitol without substantially increasing the concentration of solids in the formulation. High concentrations of solids can increase the resistance to mass transfer during lyophilization and create excessively long lyophilization cycles.

Figure 15:
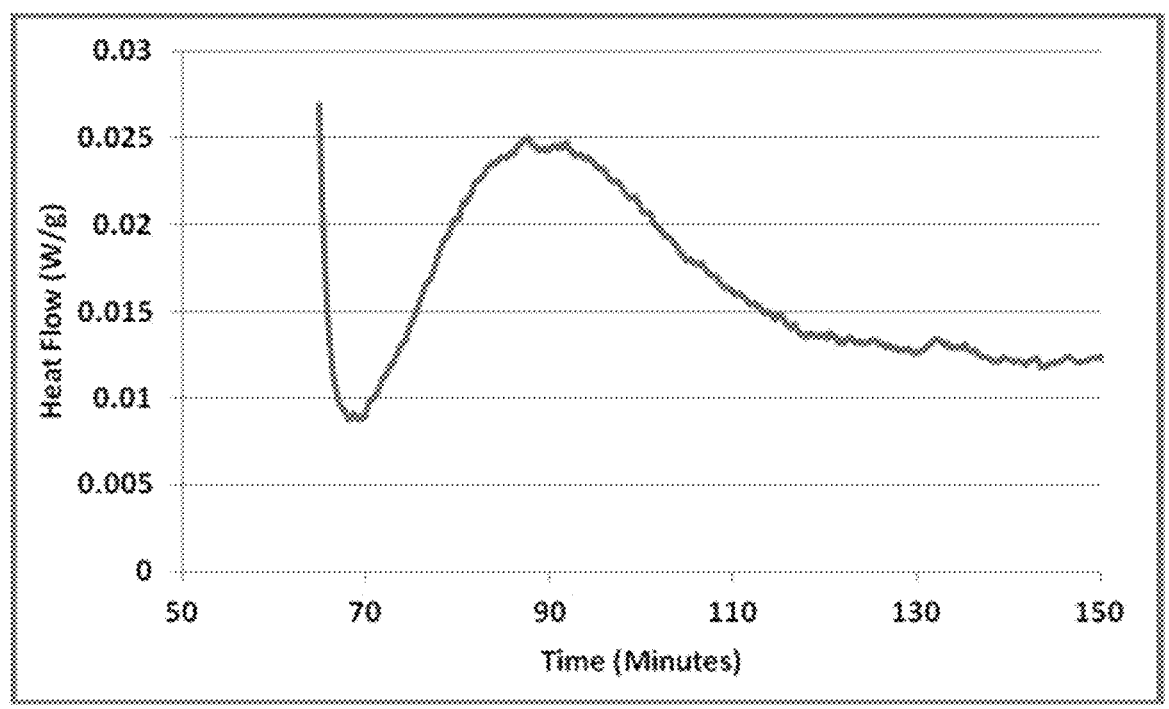
FIG. 15 is a DSC thermogram for 10 mm tris, 9.5 mm arginine, 2% sucrose, 2% mannitol, and 0.01% PS80 formulation showing the onset of crystallization of mannitol at 70 minutes (onset time of annealing) at −22° C.

Arginine concentrations were reduced in the 10 mM tris, 2% sucrose, 2% mannitol, and 0.01% PS80 formulation while keeping the mannitol concentration constant. Formulations were annealed at −15° C. to −25° C. for up to 5 hours to encourage crystallization. Crystallization of mannitol was only observed when the arginine concentration was reduced to 9.5 mM and the annealing temperature was −22° C. or greater. The crystallization of mannitol began at the onset of annealing at −22° C. (FIG. 15).

Figure 16:
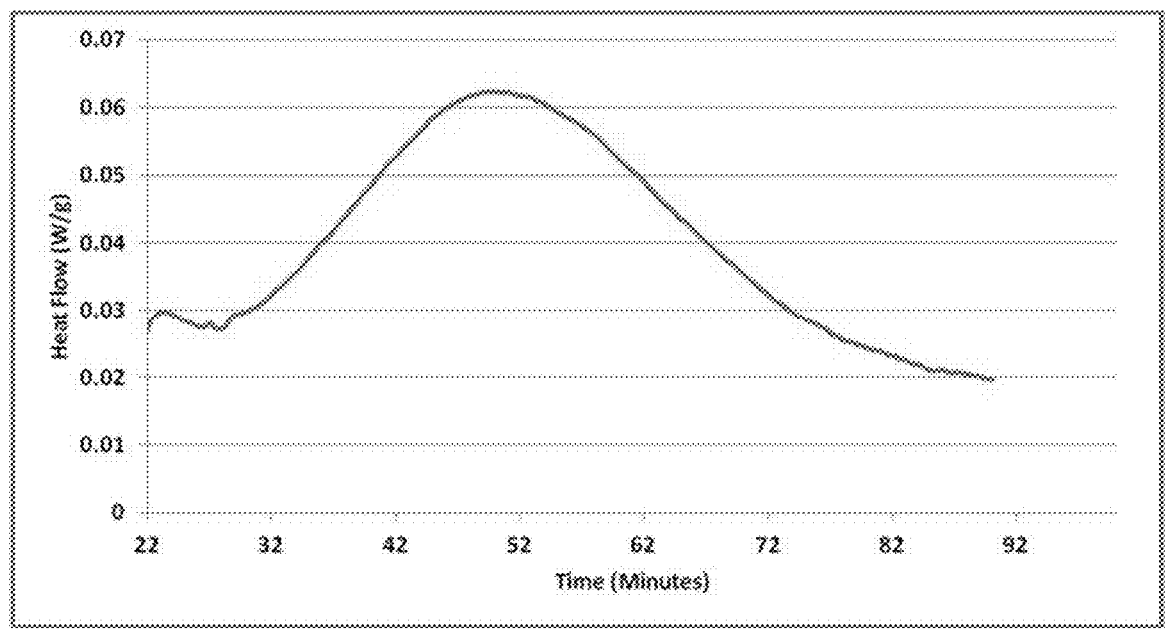
FIG. 16 is a DSC thermogram for 10 mm tris, 47.5 mm arginine, 2% sucrose, 4% mannitol, and 0.01% PS80 formulation showing a the onset of crystallization of mannitol at 30 minutes at −25° C.

The onset of crystallization for mannitol occurs after 30 minutes of annealing at −25° C. when the concentration is increased to 4% and the arginine concentration is decreased from 95 mM to 47.5 mM (FIG. 16). The lower annealing temperatures were investigated because changes to the appearance of the lyophilized cakes were observed when annealing occurred at higher temperatures. Changes to the appearance included cake shrinkage when annealing was conducted at −15° C.

The crystallization of mannitol, when using a concentration of 2% in the formulation, is delayed or prevented when the concentration of arginine is greater than 47.5 mM. The maximum concentration of arginine that can be included in the formulation without affecting the crystallization of mannitol is 47.5 mM. This statement was confirmed using lyophilization experiments that were conducted using the placebo formulation with 2% mannitol and 47.5 mM, 71 mM, or 85.5 mM arginine. Samples prepared with 47.5 mM arginine were pharmaceutically acceptable, but samples prepared with more arginine exhibited collapse. Increasing the concentration of mannitol can increase the likelihood of crystallization. Annealing of the frozen solution is required to promote crystallization when increasing the concentration of mannitol to 4% and 5% when the concentration of arginine was greater than 47.5 mM.

Figure 17:
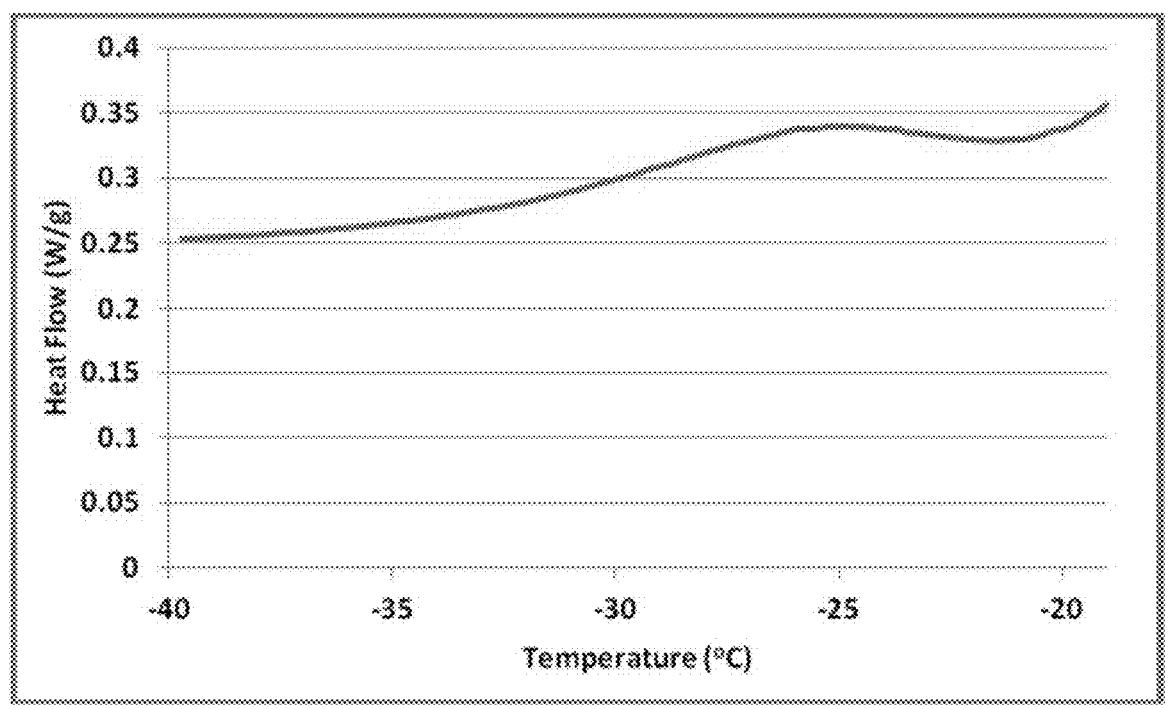
FIG. 17 is a DSC crystallization exotherm for mannitol when the 10 mm tris, 47.5 mm arginine, 2% sucrose, 5% mannitol, and 0.01% PS80 solution is cooled at 1° C./min to −40° C.

Mannitol readily crystallized in formulations containing 5% mannitol and 47.5 mM arginine. A formulation containing 10 mM tris, 47.5 mM arginine, 2% sucrose, 5% mannitol, and 0.01% PS80 was cooled slowly to −40° C. at 1° C./min (FIG. 17). The crystallization exotherm for mannitol was observed during the cooling step when the formulation was cooled at 1° C./min.

Figure 18:
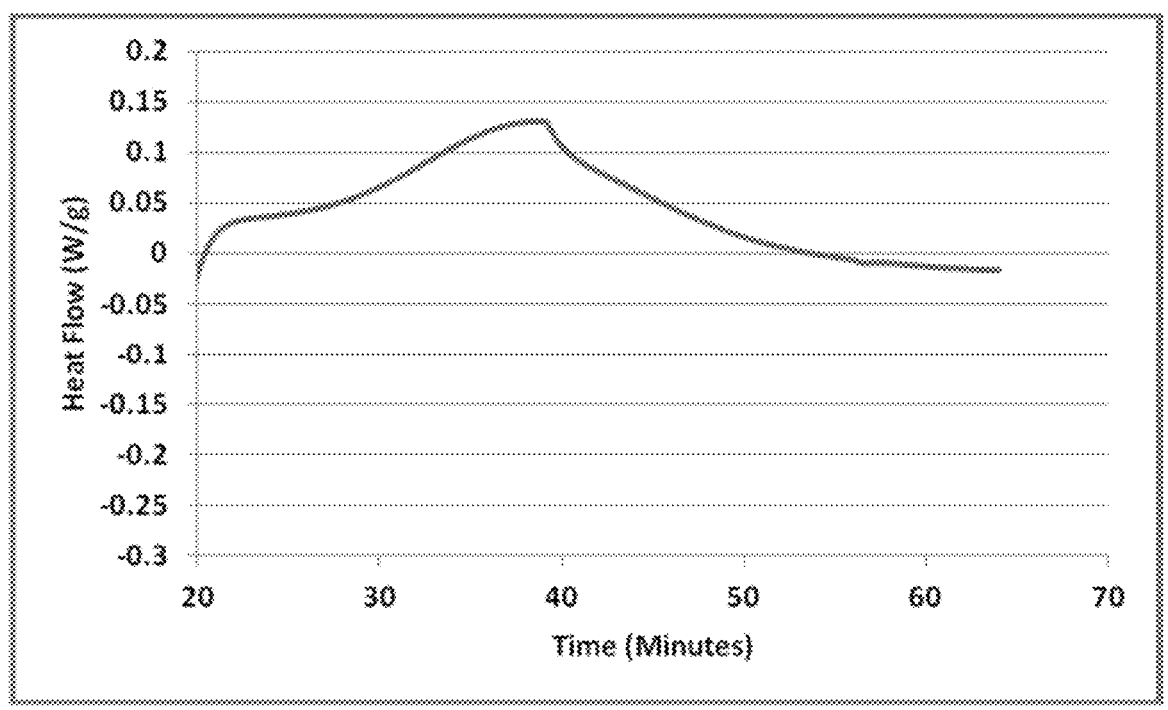
FIG. 18 shows DSC crystallization exotherm for mannitol when the 10 mm tris, 47.5 mm arginine, 2% sucrose, 5% mannitol, and 0.01% PS80 solution is annealed at −25° C. the onset of crystallization is approximately 23 minutes.

A sample of the formulation was cooled quickly (cooled faster than 10° C./min) to −40° C. and then annealed at −25° C. (FIG. 18). Mannitol crystallized after 23 minutes when the solution was annealed at −25° C. The experiments demonstrate that mannitol will readily crystallize in the formulation as long as the arginine concentration is less than 47.5 mM.

Thermal analysis data support that mannitol at a concentration of 4% or greater will readily crystallize in a reasonable timeframe during a lyophilization process if the arginine concentration is 47.5 mM or less.

2. Lyophilization

Lyophilization studies were conducted concurrently with thermal analysis experiments. Placebo solutions prepared with 10 mM tris, 9.5 mM to 23.75 mM arginine, 2% sucrose, and 2% to 4% mannitol, or 10 mM tris with 47.5 mM arginine with or without 4% sucrose. A formulation containing 10 mM tris, 47.5 mM arginine, 2% sucrose, and 5% mannitol was also included. The solutions were filled into 20 mL vials using 3 mL solution per vial. A conservative, non-conventional lyophilization cycle was used to determine if acceptable cakes could be produced. The samples were cooled to −20° C. at 1° C./min, annealed for 3 hours, cooled to −40° C. at 1° C./min, and held for 2 hours. The vacuum was initiated at 100 mTorr and the shelf temperature was ramped to −30° C. at 0.5° C./min. Samples were held at −30° C. until the Pirani gauge value matched the capacitance manometer (CM) value and then advanced to secondary drying at 25° C. at 0.5° C./min. Secondary drying was complete when the Pirani gauge value matched the CM value. Primary drying was complete after approximately 30 hours and secondary drying required only a couple of hours.

Samples prepared with tris and arginine alone exhibited complete collapse and those that included 4% sucrose exhibited cake shrinkage.

All formulations containing 47.5 mM arginine or less and 2% to 5% of mannitol appeared with acceptable cakes.

Studies were included to test the effect of annealing during the cooling ramp using a 10 mL fill volume. The studies used samples prepared with 10 mM tris, 2% sucrose, with 23.75 mM and 47.5 mM arginine, and 2% to 5% mannitol. The solution were cooled at 1° C./min to −25° C., held for 3 hours, the vacuum was initiated at 100 mTorr, and the shelf temperature was increased to −20° C. at 0.5° C./min. The samples were dried at −20° C. and the shelf was warmed to 25° C. for secondary drying. All samples appeared acceptable with no evidence of collapse.

The same formulations were used to examine the effect of cooling rate on the appearance of the lyophilized cakes. One set of samples was cooled to −25° C. at 1° C./min and annealed for 3 hours. The second set of samples was cooled to −25° C. at 5° C./min and annealed for 3 hours. The sets of samples were combined in a single dryer and lyophilized at −30° C. for primary drying followed by 25° C. for secondary drying.

All samples appeared acceptable with no evidence of collapse. The data support that cooling rates between 1° C./min and 5° C./min do not affect the appearance of the samples.

Solubility studies conducted by the client supported that the protein would remain soluble in the solution if the concentration of arginine was 36 mM or greater in the pH range of 7.5 to 8.2. It was decided to use a solution that contained 45 mM arginine because it would ensure complete solubility of the protein while also being well below the concentration that would prevent the crystallization of mannitol. The mannitol concentration was chosen as 5% to ensure that it readily crystallized during the cycle. Therefore, the best formulation candidate was 10 mM tris, 10 mg/mL or 25 mg/mL r-Antidote, 45 mM arginine, 2% sucrose, 5% mannitol, with 0.01% PS80 prepared at pH 7.8.

The lyophilization studies completed with placebo solutions demonstrated that acceptable cakes could be produced when the arginine concentration was 47.5 mM or less with 2% mannitol or greater. The solutions were lyophilized using a shelf temperature as high as −20° C. with no evidence of collapse. Samples were annealed at −20° C. for 3 hours during the cooling step or after the freezing step at −40° C. with no effect on the appearance of the cakes. The conservative and conventional approach is to first freeze samples at −40° C. followed by an annealing step with primary drying. This approach was chosen for the lyophilization cycle. Primary drying was conducted after the annealing step at −20° C. followed by increasing the shelf temperature at 0.5° C./min to 25° C. for secondary drying. Subsequent lyophilization development studies focused on the appropriate secondary drying shelf temperature and duration.

The goals for development of the lyophilized formulation included (1) protein concentration of at least 10 mg/mL; (2) improved stability at 2-8° C.; (3) reconstitution time of ≤5 min; and (4) robust lyophilization process.

Several rounds of formulation screening were performed to evaluate the effect of individual variables on protein stability (both as a lyophilized cake and in solution) and solubility at 5° C. A conservative lyophilization cycle was used during the formulation screening. lyophilization process development was performed in parallel.

The tests demonstrated that, in terms of protein concentration, higher concentration (e.g., 25 mg/mL) solutions were less stable than lower ones (e.g., 10 mg/mL) after 2 days at room temperature (i.e., greater increase in total aggregates by SEC and in % beta peak by RP-HPLC). The optimum pH for r-Antidote stability (lyophilized product and in solution) was confirmed to be pH 7.80±0.3.

No significant difference in stability was observed between tris and phosphate buffer in presence of other stabilizing components (i.e., sucrose and arginine).

In terms of stabilizer type and concentration, both 2% and 4% w/w sucrose provided a good stabilizing effect. An arginine concentration of ≥36 mM is required to maintain solubility of the r-Antidote at ≥50 mg/mL at 5° C., pH 7.80±0.3.

A crystalline component (bulking agent), mannitol, at a concentration of ≥4% w/w (in presence of 10 mM tris, 2% w/w sucrose, 45 mM arginine) was important to avoid cake collapse during primary drying. Further, the presence of a small amount of polysorbate 80 is critical to ensure r-Antidote stability in solution under shear conditions (shaking at room temperature).

The composition shown below exemplifies a suitable solution for lyophilization.

TABLE 8.3

Composition of r-Antidote for Injection 50 mg/Vial [2]

| Ingredients | Function | Quantity per Unit | Concentration after Reconstitution |
|---|---|---|---|
| r-Antidote | Active Ingredient | 50 mg | 10 mg/mL |
| Tris (Tromethamine) | Buffer | 6.1 mg | 10 mM |
| Sucrose | Stabilizer | 100 mg | 2% |
| Mannitol | Bulking agent | 250 mg | 5% |
| L-Arginine Hydrochloride | Stabilizer | 47.4 mg | 45 mM |
| Hydrochloric acid | For pH adjustment | QS to pH 7.80 ± 0.1 | |
| Polysorbate 80 | Surfactant and Stabilizer | 0.5 mg | 0.01% w/v |
| Water for Injection [1] | Vehicle | QS to 5 mL [1] | |
| pH | | | 7.8 |

[1] Removed during lyophilization.
[2] To be reconstituted with 4.70 mL Sterile Water for Injection (SWFI).

The lyophilized formulation improves the stability of the r-Antidote drug product and can be stored at 2-8° C. The following table compares the compositions of the frozen liquid drug product and the reconstituted lyophilized drug product. Examples of the composition of a 100 mg/vial and 400 mg/vial lyophilized drug product and example reconstituted compositions are presented.

TABLE 8.4

Formulation of r-Antidote Frozen Liquid Drug Product, for Injection, 3 mg/mL

| Ingredients | Amount per Vial | Amount (mg/mL) |
|---|---|---|
| r-Antidote | 30 mg | 3 mg/mL |
| Tris | 12.1 mg | 1.21 mg/mL (10 mM) |
| L-Arginine Hydrochloride | 200 mg | 20.0 mg/mL (95 mM) |
| Sucrose | 400 mg | 40.0 mg/mL (4% w/w) |
| Polysorbate 80 | 1.0 mg | 0.1 mg/mL (0.01% w/w) |
| Water for Injection | QS to 10 g | |
| Hydrochloric Acid solution, 1N | QS to pH = 7.8 | |
| Sodium Hydroxide solution, 1N | QS to pH = 7.8 | |
| pH | 7.8 ± 0.3 | 7.8 ± 0.3 |

TABLE 8.5

Formulation of r-Antidote Lyophilized Drug Product, for Injection, 50 mg/vial

| Ingredients | Amount per Vial | Amount (mg/mL) After Reconstitution |
|---|---|---|
| r-Antidote | 50 mg | 10 mg/mL |
| Tris | 6.1 mg | 1.22 mg/mL (10 mM) |
| L-Arginine Hydrochloride | 47.4 mg | 9.48 mg/mL (45 mM) |
| Sucrose | 100 mg | 20 mg/mL (2% w/w) |
| Mannitol | 250 mg | 50 mg/mL (5% w/w) |
| Polysorbate 80 | 0.5 mg | 0.1 mg/mL (0.01% w/w) |
| Sterile Water for Injection | QS to 5 mL, removed during lyophilization process | |
| Hydrochloric Acid | QS to pH = 7.8 | |
| pH | 7.8 ± 0.3 | 7.8 ± 0.3 |

TABLE 8.6

Formulation of r-Antidote Lyophilized Drug Product, for Injection, 100 mg/vial

| Ingredients | Amount per Vial | Amount (mg/mL) After Reconstitution |
|---|---|---|
| r-Antidote | 100 mg | 10 mg/mL |
| Tris | 12.1 mg | 1.22 mg/mL (10 mM) |
| L-Arginine Hydrochloride | 94.8 mg | 9.48 mg/mL (45 mM) |
| Sucrose | 200 mg | 20 mg/mL (2% w/w) |
| Mannitol | 500 mg | 50 mg/mL (5% w/w) |
| Polysorbate 80 | 1.0 mg | 0.1 mg/mL (0.01% w/v) |
| Sterile Water for Injection | QS to 10 mL, removed during lyophilization process | |
| Hydrochloric Acid | QS to pH = 7.8 | |
| pH | 7.8 ± 0.3 | 7.8 ± 0.3 |

TABLE 8.7

Formulation of r-Antidote Lyophilized Drug Product, for Injection, 400 mg/vial

| Ingredients | Amount per Vial | Amount (mg/mL) After Reconstitution (40 mL total) |
|---|---|---|
| r-Antidote | 400 mg | 10 mg/mL |
| Tris | 12.1 mg | 0.30 mg/mL (2.5 mM) |
| Tris HCl | 15.8 mg | 0.39 mg/mL (2.5 mM) |
| L-Arginine Hydrochloride | 189.6 mg | 4.7 mg/mL (22.5 mM) |
| Sucrose | 400 mg | 10 mg/mL (1% w/v) |
| Mannitol | 1000 mg | 25 mg/mL (2.5% w/v) |
| Polysorbate 80 | 2.0 mg | 0.1 mg/mL (0.01% w/v) |
| Sterile Water for Injection | QS to 20 mL, removed during lyophilization process | |
| pH | 7.8 ± 0.3 | 7.8 ± 0.3 |

Freeze drying microscopy was performed on two different formulations. Approximately 0.15 mL of solution was dispensed into a glass cell which was placed on a temperature-controlled freeze-drying stage. Thermocouples were placed onto the bottom and center of the cell to monitor sample temperatures. The liquid was cooled at a rate of 0.5° C/min to −50° C., annealed at −20° C. for 1 hour, and refrozen to −50° C. The chamber was evacuated and heated at a rate of 0.5° C/min. Based on this collapse temperature, combinations of freeze drying temperatures and pressures that result in product temperatures below the collapse temperature will produce a cake with no collapse. For example product temperatures of up to 20° C. with 100 mTorr could be used to produce a cake with no collapse.

| Formulation | Collapse Temperature (° C.) |
|---|---|
| 10 mg/mL r-Antidote, 10 mM Tris, 45 mM L-Arginine HCl, 2% w/v Sucrose, 5% w/v Mannitol, 0.01% polysorbate 80, pH 7.8 | −15 |
| 20 mg/mL r-Antidote, 10 mM Tris, 45 mM L-Arginine HCl, 2% w/v Sucrose, 5% w/v Mannitol, 0.01% polysorbate 80, pH 7.8 | −14 |

After reconstitution r-Antidote for injection with SWFI, 50 mg/vial is pH 7.8, with an osmolality of ~480 mOsm/kg. Therefore the reconstituted DP is acceptable for intravenous administration.

r-Antidote BDS is formulated at 3.0 mg/mL in 10 mM Tris, pH 7.8±0.3, 4% sucrose, 95 mM arginine and stored frozen at −60° C. or colder. The manufacture of r-Antidote for Injection consists of the thawing and pooling of the 3 mg/mL r-Antidote BDS, ultra filtration/diafiltration against formulation buffer (10 mM tris, 2% sucrose, 5% mannitol, 45 mL arginine HCl, pH 7.8) to a final concentration of 10 mg/mL, spiking of polysorbate 80 to 0.01% w/w, aseptic filling, lyophilization, stoppering, capping and labeling into the r-Antidote for Injection container closure system.

The r-Antidote for injection manufacturing process utilizes procedures which were developed for the production of other sterile liquid drug products. The method of sterilization used to produce r-Antidote for Injection is 0.2 µm filtration. The r-Antidote is heat labile; therefore 0.2 μm filtration is the most appropriate means of producing sterile r-Antidote for injection.

The lyophilization process was developed using a rational approach based on an understanding of the physical nature of the formulation components at different stages of the lyophilization cycle. Thermal characterization methods including differential scanning calorimetry (DSC) and freeze dry microscopy (FDM) were used to measure Tg' (glass transition temperature of the frozen concentrate) and Tc (collapse temperature during primary drying). The cycle shown in the table below was selected for lyophilization of prototype batch J7128. The annealing step allows crystallization of mannitol to ensure that product temperature does not fall below collapse temperature during primary drying. The primary drying temperature was selected to avoid cake collapse with a reasonable duration of primary drying. The 2-step secondary drying condition was developed to produce a lyophilized DP with a moisture level of <1% (see, e.g., Table 6).

The invention claimed is:

1. A method for preparing a lyophilized formulation, comprising lyophilizing an aqueous solution comprising about 45 mM arginine, from 1% to 3% sucrose (w/v), from 2% to 8% mannitol (w/v), from about 0.01% to about 0.02% (w/v) polysorbate 80 and at least 5 mg/mL of a two-chain polypeptide comprising a first chain comprising the amino acid sequence of SEQ ID NO. 4, a second chain comprising the amino acid sequence of SEQ ID NO. 5, and a disulfide bond between a first Cysteine residue at position 98 (Cys98) of SEQ ID NO. 4 and a second Cysteine residue at position 108 (Cys108) of SEQ ID NO. 5, wherein the aqueous solution has a pH from 7.7 to 7.9.

2. The method of claim 1, wherein the aqueous solution comprises about 45 mM arginine, from 1.5% to 2.5% sucrose (w/v), from 4.5% to 5.5% mannitol (w/v), from about 0.01% to about 0.02% (w/v) polysorbate 80 and at least 10 mg/mL of the polypeptide.

3. The method of claim 2, wherein the aqueous solution comprises at least 18 mg/mL of the polypeptide.

4. The method of claim 1, wherein the polypeptide comprises at least an intra-chain disulfide bond for each of the first and second chains.

5. The method of claim 1, wherein the aqueous solution comprises about 45 mM arginine, about 2% sucrose (w/v), about 5% mannitol (w/v), about 0.01% polysorbate 80 and about 10 mg/mL of the two-chain polypeptide, wherein the aqueous solution has a pH of about 7.8.

6. The method of claim 1, wherein the aqueous solution comprises about 45 mM arginine, about 2% sucrose (w/v), about 5% mannitol (w/v), about 0.02% polysorbate 80 and about 20 mg/mL of the two-chain polypeptide, wherein the aqueous solution has a pH of about 7.8.

7. The method of claim 1, wherein the lyophilized formulation comprises L-arginine HCl:sucrose:mannitol in a weight ratio of the range of (0.5-1.4):(1-3):(2-8).

8. The method of claim 1, wherein the lyophilized formulation comprises L-arginine HCl:sucrose:mannitol in a weight ratio of the range of (0.9-1):(1.5-2.5):(4.5-5.5).

9. The method of claim 1, wherein the lyophilized formulation comprises L-arginine HCl:sucrose:mannitol in a weight ratio of about 0.95:2:5.

* * * * *

SEQUENCE LISTING

```
<160> NUMBER OF SEQ ID NOS: 6

<210> SEQ ID NO 1
<211> LENGTH: 448
<212> TYPE: PRT
<213> ORGANISM: Homo sapiens

<400> SEQUENCE: 1

Ala Asn Ser Phe Leu Glu Glu Met Lys Lys Gly His Leu Glu Arg Glu
1               5                   10                  15

Cys Met Glu Glu Thr Cys Ser Tyr Glu Glu Ala Arg Glu Val Phe Glu
            20                  25                  30

Asp Ser Asp Lys Thr Asn Glu Phe Trp Asn Lys Tyr Lys Asp Gly Asp
        35                  40                  45

Gln Cys Glu Thr Ser Pro Cys Gln Asn Gln Gly Lys Cys Lys Asp Gly
    50                  55                  60

Leu Gly Glu Tyr Thr Cys Thr Cys Leu Glu Gly Phe Glu Gly Lys Asn
65                  70                  75                  80

Cys Glu Leu Phe Thr Arg Lys Leu Cys Ser Leu Asp Asn Gly Asp Cys
                85                  90                  95

Asp Gln Phe Cys His Glu Glu Gln Asn Ser Val Val Cys Ser Cys Ala
            100                 105                 110

Arg Gly Tyr Thr Leu Ala Asp Asn Gly Lys Ala Cys Ile Pro Thr Gly
        115                 120                 125

Pro Tyr Pro Cys Gly Lys Gln Thr Leu Glu Arg Arg Lys Arg Ser Val
    130                 135                 140

Ala Gln Ala Thr Ser Ser Ser Gly Glu Ala Pro Asp Ser Ile Thr Trp
145                 150                 155                 160

Lys Pro Tyr Asp Ala Ala Asp Leu Asp Pro Thr Glu Asn Pro Phe Asp
                165                 170                 175

Leu Leu Asp Phe Asn Gln Thr Gln Pro Glu Arg Gly Asp Asn Asn Leu
            180                 185                 190

Thr Arg Ile Val Gly Gly Gln Glu Cys Lys Asp Gly Glu Cys Pro Trp
        195                 200                 205

Gln Ala Leu Leu Ile Asn Glu Glu Asn Glu Gly Phe Cys Gly Gly Thr
    210                 215                 220

Ile Leu Ser Glu Phe Tyr Ile Leu Thr Ala Ala His Cys Leu Tyr Gln
225                 230                 235                 240

Ala Lys Arg Phe Lys Val Arg Val Gly Asp Arg Asn Thr Glu Gln Glu
                245                 250                 255

Glu Gly Gly Glu Ala Val His Glu Val Glu Val Val Ile Lys His Asn
            260                 265                 270

Arg Phe Thr Lys Glu Thr Tyr Asp Phe Asp Ile Ala Val Leu Arg Leu
        275                 280                 285

Lys Thr Pro Ile Thr Phe Arg Met Asn Val Ala Pro Ala Cys Leu Pro
    290                 295                 300
```

```
Glu Arg Asp Trp Ala Glu Ser Thr Leu Met Thr Gln Lys Thr Gly Ile
305                 310                 315                 320

Val Ser Gly Phe Gly Arg Thr His Glu Lys Gly Arg Gln Ser Thr Arg
                325                 330                 335

Leu Lys Met Leu Glu Val Pro Tyr Val Asp Arg Asn Ser Cys Lys Leu
            340                 345                 350

Ser Ser Ser Phe Ile Ile Thr Gln Asn Met Phe Cys Ala Gly Tyr Asp
        355                 360                 365

Thr Lys Gln Glu Asp Ala Cys Gln Gly Asp Ser Gly Gly Pro His Val
370                 375                 380

Thr Arg Phe Lys Asp Thr Tyr Phe Val Thr Gly Ile Val Ser Trp Gly
385                 390                 395                 400

Glu Gly Cys Ala Arg Lys Gly Lys Tyr Gly Ile Tyr Thr Lys Val Thr
                405                 410                 415

Ala Phe Leu Lys Trp Ile Asp Arg Ser Met Lys Thr Arg Gly Leu Pro
            420                 425                 430

Lys Ala Lys Ser His Ala Pro Glu Val Ile Thr Ser Ser Pro Leu Lys
        435                 440                 445
```

<210> SEQ ID NO 2
<211> LENGTH: 365
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 2

```
Ala Asn Ser Phe Leu Phe Trp Asn Lys Tyr Lys Asp Gly Asp Gln Cys
1               5                   10                  15

Glu Thr Ser Pro Cys Gln Asn Gly Lys Cys Lys Asp Gly Leu Gly
            20                  25                  30

Glu Tyr Thr Cys Thr Cys Leu Glu Gly Phe Glu Gly Lys Asn Cys Glu
        35                  40                  45

Leu Phe Thr Arg Lys Leu Cys Ser Leu Asp Asn Gly Asp Cys Asp Gln
50                  55                  60

Phe Cys His Glu Glu Gln Asn Ser Val Val Cys Ser Cys Ala Arg Gly
65                  70                  75                  80

Tyr Thr Leu Ala Asp Asn Gly Lys Ala Cys Ile Pro Thr Gly Pro Tyr
                85                  90                  95

Pro Cys Gly Lys Gln Thr Leu Glu Arg Arg Lys Arg Arg Lys Arg Ile
            100                 105                 110

Val Gly Gly Gln Glu Cys Lys Asp Gly Glu Cys Pro Trp Gln Ala Leu
        115                 120                 125

Leu Ile Asn Glu Glu Asn Glu Gly Phe Cys Gly Gly Thr Ile Leu Ser
130                 135                 140

Glu Phe Tyr Ile Leu Thr Ala Ala His Cys Leu Tyr Gln Ala Lys Arg
145                 150                 155                 160

Phe Lys Val Arg Val Gly Asp Arg Asn Thr Glu Gln Glu Glu Gly Gly
                165                 170                 175

Glu Ala Val His Glu Val Glu Val Val Ile Lys His Asn Arg Phe Thr
            180                 185                 190

Lys Glu Thr Tyr Asp Phe Asp Ile Ala Val Leu Arg Leu Lys Thr Pro
        195                 200                 205

Ile Thr Phe Arg Met Asn Val Ala Pro Ala Cys Leu Pro Glu Arg Asp
```

```
                    210                 215                 220
Trp Ala Glu Ser Thr Leu Met Thr Gln Lys Thr Gly Ile Val Ser Gly
225                 230                 235                 240

Phe Gly Arg Thr His Glu Lys Gly Arg Gln Ser Thr Arg Leu Lys Met
            245                 250                 255

Leu Glu Val Pro Tyr Val Asp Arg Asn Ser Cys Lys Leu Ser Ser Ser
                260                 265                 270

Phe Ile Ile Thr Gln Asn Met Phe Cys Ala Gly Tyr Asp Thr Lys Gln
            275                 280                 285

Glu Asp Ala Cys Gln Gly Asp Ala Gly Gly Pro His Val Thr Arg Phe
        290                 295                 300

Lys Asp Thr Tyr Phe Val Thr Gly Ile Val Ser Trp Gly Glu Gly Cys
305                 310                 315                 320

Ala Arg Lys Gly Lys Tyr Gly Ile Tyr Thr Lys Val Thr Ala Phe Leu
                325                 330                 335

Lys Trp Ile Asp Arg Ser Met Lys Thr Arg Gly Leu Pro Lys Ala Lys
            340                 345                 350

Ser His Ala Pro Glu Val Ile Thr Ser Ser Pro Leu Lys
            355                 360                 365

<210> SEQ ID NO 3
<211> LENGTH: 359
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 3

Ala Asn Ser Phe Leu Phe Trp Asn Lys Tyr Lys Asp Gly Asp Gln Cys
1               5                   10                  15

Glu Thr Ser Pro Cys Gln Asn Gln Gly Lys Cys Lys Asp Gly Leu Gly
            20                  25                  30

Glu Tyr Thr Cys Thr Cys Leu Glu Gly Phe Glu Gly Lys Asn Cys Glu
        35                  40                  45

Leu Phe Thr Arg Lys Leu Cys Ser Leu Asp Asn Gly Asp Cys Asp Gln
    50                  55                  60

Phe Cys His Glu Glu Gln Asn Ser Val Val Cys Ser Cys Ala Arg Gly
65                  70                  75                  80

Tyr Thr Leu Ala Asp Asn Gly Lys Ala Cys Ile Pro Thr Gly Pro Tyr
                85                  90                  95

Pro Cys Gly Lys Gln Thr Leu Glu Arg Ile Val Gly Gly Gln Glu Cys
            100                 105                 110

Lys Asp Gly Glu Cys Pro Trp Gln Ala Leu Leu Ile Asn Glu Glu Asn
        115                 120                 125

Glu Gly Phe Cys Gly Gly Thr Ile Leu Ser Glu Phe Tyr Ile Leu Thr
    130                 135                 140

Ala Ala His Cys Leu Tyr Gln Ala Lys Arg Phe Lys Val Arg Val Gly
145                 150                 155                 160

Asp Arg Asn Thr Glu Gln Glu Glu Gly Gly Glu Ala Val His Glu Val
                165                 170                 175

Glu Val Val Ile Lys His Asn Arg Phe Thr Lys Glu Thr Tyr Asp Phe
            180                 185                 190

Asp Ile Ala Val Leu Arg Leu Lys Thr Pro Ile Thr Phe Arg Met Asn
        195                 200                 205
```

```
Val Ala Pro Ala Cys Leu Pro Glu Arg Asp Trp Ala Glu Ser Thr Leu
    210                 215                 220

Met Thr Gln Lys Thr Gly Ile Val Ser Gly Phe Gly Arg Thr His Glu
225                 230                 235                 240

Lys Gly Arg Gln Ser Thr Arg Leu Lys Met Leu Glu Val Pro Tyr Val
                245                 250                 255

Asp Arg Asn Ser Cys Lys Leu Ser Ser Ser Phe Ile Ile Thr Gln Asn
            260                 265                 270

Met Phe Cys Ala Gly Tyr Asp Thr Lys Gln Glu Asp Ala Cys Gln Gly
        275                 280                 285

Asp Ala Gly Gly Pro His Val Thr Arg Phe Lys Asp Thr Tyr Phe Val
    290                 295                 300

Thr Gly Ile Val Ser Trp Gly Glu Gly Cys Ala Arg Lys Gly Lys Tyr
305                 310                 315                 320

Gly Ile Tyr Thr Lys Val Thr Ala Phe Leu Lys Trp Ile Asp Arg Ser
                325                 330                 335

Met Lys Thr Arg Gly Leu Pro Lys Ala Lys Ser His Ala Pro Glu Val
            340                 345                 350

Ile Thr Ser Ser Pro Leu Lys
            355

<210> SEQ ID NO 4
<211> LENGTH: 105
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 4

Ala Asn Ser Phe Leu Phe Trp Asn Lys Tyr Lys Asp Gly Asp Gln Cys
1               5                   10                  15

Glu Thr Ser Pro Cys Gln Asn Gln Gly Lys Cys Lys Asp Gly Leu Gly
            20                  25                  30

Glu Tyr Thr Cys Thr Cys Leu Glu Gly Phe Glu Gly Lys Asn Cys Glu
        35                  40                  45

Leu Phe Thr Arg Lys Leu Cys Ser Leu Asp Asn Gly Asp Cys Asp Gln
    50                  55                  60

Phe Cys His Glu Glu Gln Asn Ser Val Val Cys Ser Cys Ala Arg Gly
65                  70                  75                  80

Tyr Thr Leu Ala Asp Asn Gly Lys Ala Cys Ile Pro Thr Gly Pro Tyr
                85                  90                  95

Pro Cys Gly Lys Gln Thr Leu Glu Arg
            100                 105

<210> SEQ ID NO 5
<211> LENGTH: 254
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 5

Ile Val Gly Gly Gln Glu Cys Lys Asp Gly Glu Cys Pro Trp Gln Ala
1               5                   10                  15

Leu Leu Ile Asn Glu Glu Asn Glu Gly Phe Cys Gly Gly Thr Ile Leu
            20                  25                  30
```

```
Ser Glu Phe Tyr Ile Leu Thr Ala Ala His Cys Leu Tyr Gln Ala Lys
        35                  40                  45

Arg Phe Lys Val Arg Val Gly Asp Arg Asn Thr Glu Gln Glu Glu Gly
50                  55                  60

Gly Glu Ala Val His Glu Val Glu Val Val Ile Lys His Asn Arg Phe
65                  70                  75                  80

Thr Lys Glu Thr Tyr Asp Phe Asp Ile Ala Val Leu Arg Leu Lys Thr
                85                  90                  95

Pro Ile Thr Phe Arg Met Asn Val Ala Pro Ala Cys Leu Pro Glu Arg
                100                 105                 110

Asp Trp Ala Glu Ser Thr Leu Met Thr Gln Lys Thr Gly Ile Val Ser
        115                 120                 125

Gly Phe Gly Arg Thr His Glu Lys Gly Arg Gln Ser Thr Arg Leu Lys
        130                 135                 140

Met Leu Glu Val Pro Tyr Val Asp Arg Asn Ser Cys Lys Leu Ser Ser
145                 150                 155                 160

Ser Phe Ile Ile Thr Gln Asn Met Phe Cys Ala Gly Tyr Asp Thr Lys
                165                 170                 175

Gln Glu Asp Ala Cys Gln Gly Asp Ala Gly Gly Pro His Val Thr Arg
                180                 185                 190

Phe Lys Asp Thr Tyr Phe Val Thr Gly Ile Val Ser Trp Gly Glu Gly
        195                 200                 205

Cys Ala Arg Lys Gly Lys Tyr Gly Ile Tyr Thr Lys Val Thr Ala Phe
        210                 215                 220

Leu Lys Trp Ile Asp Arg Ser Met Lys Thr Arg Gly Leu Pro Lys Ala
225                 230                 235                 240

Lys Ser His Ala Pro Glu Val Ile Thr Ser Ser Pro Leu Lys
                245                 250

<210> SEQ ID NO 6
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 6

Arg Lys Arg Arg Lys Arg
1               5
```